US012753214B2

(12) United States Patent
Corrigall et al.

(10) Patent No.: US 12,753,214 B2
(45) Date of Patent: Oct. 6, 2026

(54) PROTEIN WITH ANTI-INFLAMMATORY PROPERTIES

(71) Applicant: REVOLO BIOTHERAPEUTICS LIMITED, Great Shelford (GB)

(72) Inventors: Valerie Mary Corrigall, Tadworth (GB); Gabriel Stavros Panayi, Larnaca (CY)

(73) Assignee: Revolo Biotherapeutics Limited, Great Shelford (GB)

( * ) Notice: Subject to any disclaimer, the term of this patent is extended or adjusted under 35 U.S.C. 154(b) by 476 days.

(21) Appl. No.: 17/086,356

(22) Filed: Oct. 31, 2020

(65) Prior Publication Data

US 2021/0238239 A1 Aug. 5, 2021

Related U.S. Application Data

(62) Division of application No. 16/007,742, filed on Jun. 13, 2018, now Pat. No. 10,858,409.

(51) Int. Cl.

*C07K 14/00* (2006.01)
*A61K 38/00* (2006.01)
*A61P 19/02* (2006.01)
*C07K 14/47* (2006.01)
*A61K 38/26* (2006.01)

(52) U.S. Cl.

CPC .......... *C07K 14/4702* (2013.01); *A61P 19/02* (2018.01); *A61K 38/00* (2013.01); *A61K 38/26* (2013.01)

(58) Field of Classification Search

None

See application file for complete search history.

(56) References Cited

U.S. PATENT DOCUMENTS

| | | | |
|---|---|---|---|
| 2004/0116344 A1 | 6/2004 | Panayi et al. | |
| 2009/0118173 A1 | 5/2009 | Van et al. | |
| 2010/0041074 A1 | 2/2010 | Kimura | |
| 2013/0259862 A1 | 10/2013 | Nishimura et al. | |
| 2014/0294902 A1 | 10/2014 | Bhandari et al. | |
| 2018/0243244 A1 | 8/2018 | Kwon et al. | |
| 2019/0382457 A1 | 12/2019 | Corrigall et al. | |

FOREIGN PATENT DOCUMENTS

| | | | |
|---|---|---|---|
| CN | 1322213 | A | 11/2001 |
| CN | 1537173 | A | 10/2004 |
| CN | 104704126 | A | 6/2015 |
| EP | 3338787 | | 6/2018 |
| JP | 2003523167 | A | 8/2003 |
| JP | 2008536904 | A | 9/2008 |
| WO | WO 20021995 | | 4/2000 |
| WO | 02072133 | A1 | 9/2002 |
| WO | 2006073446 | A2 | 7/2006 |
| WO | WO 2006111720 | | 10/2006 |
| WO | WO 2015131245 | | 9/2015 |
| WO | WO 2017030292 | | 2/2017 |
| WO | 2017144897 | A1 | 8/2017 |
| WO | 2019239126 | A1 | 12/2019 |

OTHER PUBLICATIONS

Miller et al. RBP-J-Regulated mirR-182 proteins TNF-alpha induces osteoclastogenesis. Abstract. Journal of Immunology, vol. 196/No. 12, pp. 4977-4986, (2016). (Year: 2016).*

Arnau et al. Current strategies for the use of affinity tags and tag removal for the purification of recombinant proteins. Protein Expression and Purification vol. 48:1-13 (2006). (Year: 2006).

Bigazzi et al. Introduction to Review Series on Animal Models of Human Disease. Clinical Immunology and Immunopathology, vol. 74 No. 1, p. 1 (Jan. 1995). (Year: 1995).

Freshney. Culture of Animal Cells, A Manual of Basic Technique, Alan R. Liss, Inc., 1983, New York, p. 4. (Year: 1983).

PCT International Search Report and Written Opinion in International Application No. PCT/GB2019/051622, dated Sep. 18, 2019, 11 pages.

Justice et al. Using the mouse to model human disease: increasing validity and reproducibility. Disease, Models & Mechanisms vol. 9:101-103 (2016). (Year: 2016).

Kim et al. The effects of Lycii Radicis Cortex on RANKL-induced osteoclast differentiation and activati on in RAW 264.7 cells. International Journal of Molecular Medicine 37:649-658; (2016). (Year: 2016).

Kirkham et al. Safety and patient response as indicated by biomarker changes to binding immunoglobulin protein in the phase I/IIA Ragula clinical trial in rheumatoid arthritis. Rheumatology, vol. 55:1993-2000 (2016). (Year: 2016).

Wakabayashi et al. Prevention of metastasis by a polyamine synthesis inhibitor in an animal bone metastasis model. Oncology, 59:75-80 (2000). (Year: 2000).

Wei et al. Characterization of the Nucleotide Binding Properties and ATPase Activity of Recombinant Hamster BiP Purified from Bacteria* The Journal of Biological Chemistry vol. 270, No. 44, Issue of Nov. 3, pp. 26670-26676 (1995) .(Year: 1995).

Yang et al. Novel Immunohistochemical Monoclonal Antibody Against Human Glucose-Regulated Protein 78. Hybridoma vol. 30, No. 6:559-562 (2011). (Year: 2011).

Zhou et al. Developments in Structural Genomics: Protein Purification and Function Interpretation. Current Genomics, vol. 5:37-48 (2004). (Year: 2004).

(Continued)

*Primary Examiner* — Bridget E Bunner
*Assistant Examiner* — Regina M DeBerry
(74) *Attorney, Agent, or Firm* — Adler Pollock & Sheehan P.C.; Michel Morency

(57) ABSTRACT

The present invention provides an isolated or recombinant protein consisting of the amino acid sequence according to SEQ ID NO: 3 or SEQ ID: NO: 4 and its use in the prevention or treatment of an inflammatory condition.

6 Claims, 26 Drawing Sheets

Specification includes a Sequence Listing.

(56) References Cited

OTHER PUBLICATIONS

International Search Report and Written Opinion for PCT Patent Application No. PCT/GB2023/050876, mailed on Aug. 22, 2023, 12 pages.
"Predicted: 78 kDa glucose-regulated protein [Galeopterus variegatus]", NCBI Reference Sequence: XP_008568189.1, Retrieved from https://www.ncbi.nlm.nih.gov/protein/XP_008568189.1?report=genbank&log$=protalign&blast_rank=12&RID=TZ5GRHUB013, Jul. 22, 2014, 2 pages.
Awad, et al., "BiP Mutants that Are Unable to Interact With Endoplasmic Reticulum DnaJ Proteins Provide Insights Into Interdomain Interactions in BiP", PNAS 105(4):1164-1169, Jan. 29, 2008.
Cha-Molstad, et al., "Amino-Terminal Arginylation Targets Endoplasmic Reticulum Chaperone BiP for Autophagy Through p62 Binding", Nature Cell Biology, 17(7):917-929, Jul. 2015.
Jiang, et al., "The Arginylation Branch of the N-End Rule Pathway Positively Regulates Cellular Autophagic Flux and Clearance of Proteotoxic Proteins", Autophagy, 12(11):2197-2212, 2016.
Liu, et al., "Research Progress of Endoplasmic Reticulum Stress And Viral Hepatitis", Medical Recapitulate, 24(2):261-265, 2018, English Abstract Only.
Magalhaes, et al., "Methods of Endotoxin Removal from Biological Preparations: A Review", Journal of Pharmacy and Pharmaceutical Sciences, 10(3):388-404, 2007.
Zhu, et al., "Down Regulated BiP Expression Improves Efficacy of Split FVIII Gene Delivery by a Dual-Vector", Chinese Journal of Biochemistry and Molecular Biology, 27(12):1161-1166, 2011, English Abstract Only.
Wei J et al., "In Vitro Dissociation of BiP-Peptide Complexes Requires a Conformational Change in BiP after ATP Binding but Does Not Require ATP Hydrolysis (•)", Journal of Biological Chemistry, 1995; 270, 26677-26682.

* cited by examiner

Native BiP amino acid sequence

MKLSLVAAML LLLSAARAEE EDKKEDVGTV VGIDLGTTYS CVGVFKNGRV EIIANDQGNR
ITPSYVAFTP EGERLIGDAA KNQLTSNPEN TVFDAKRLIG RTWNDPSVQQ DIKFLPFKVV
EKKTKPYIQV DIGGGQTKTF APEEISAMVL TKMKETAEAY LGKKVTHAVV TVPAYFNDAQ
RQATKDAGTI AGLNVMRIIN EPTAAAIAYG LDKREGEKNI LVFDLGGGTF DVSLLTIDNG
VFEVVATNGD THLGGEDFDQ RVMEHFIKLY KKKTGKDVRK DNRAVQKLRR EVEKAKRALS
SQHQARIEIE SFYEGEDFSE TLTRAKFEEL NMDLFRSTMK PVQKVLEDSD LKKSDIDEIV
LVGGSTRIPK IQQLVKEFFN GKEPSRGINP DEAVAYGAAV QAGVLSGDQD TGDLVLLDVC
PLTLGIETVG GVMTKLIPRN TVVPTKKSQI FSTASDNQPT VTIKVYEGER PLTKDNHLLG
TFDLTGIPPA PRGVPQIEVT FEIDVNGILR VTAEDKGTGN KNKITITNDQ NRLTPEEIER
MVNDAEKFAE EDKKLKERID TRNELESYAY SLKNQIGDKE KLGGKLSSED KETMEKAVEE
KIEWLESHQD ADIEDFKAKK KELEEIVQPI ISKLYGSAGP PPTGEEDTAE KDEL

SEQ ID NO: 5

FIG. 1

Primary nucleotide sequence of native BiP 1 aggtcgacgc cggccaagac agcacagaca gattgaccta ttggggtgtt tcgcgagtgt 61 gagagggaag cgccgcggcc tgtatttcta gacctgccct tcgcctggtt cgtggcgcct 121 tgtgaccccg ggcccctgcc gcctgcaagt cggaaattgc gctgtgctcc tgtgctacgg 181 cctgtggctg gactgcctgc tgctgcccaa ctggctggca agatgaagct ctccctggtg 241 gccgcgatgc tgctgctgct cagcgcggcg cgggccgagg aggaggacaa gaaggaggac 301 gtgggcacgg tggtcggcat cgacttgggg accacctact cctgcgtcgg cgtgttcaag 361 aacggccgcg tggagatcat cgccaacgat cagggcaacc gcatcacgcc gtcctatgtc 421 gccttcactc ctgaagggga acgtctgatt ggcgatgccg ccaagaacca gctcacctcc 481 aaccccgaga acacggtctt tgacgccaag cggctcatcg gccgcacgtg gaatgacccg 541 tctgtgcagc aggacatcaa gttcttgccg ttcaaggtgg ttgaaaagaa aactaaacca 601 tacattcaag ttgatattgg aggtgggcaa acaaagacat ttgctcctga agaaatttct 661 gccatggttc tcactaaaat gaaagaaacc gctgaggctt atttgggaaa gaaggttacc 721 catgcagttg ttactgtacc agcctatttt aatgatgccc aacgccaagc aaccaaagac 781 gctggaacta ttgctggcct aaatgttatg aggatcatca acgagcctac ggcagctgct 841 attgcttatg gcctggataa gagggagggg gagaagaaca tcctggtgtt tgacctgggt 901 ggcggaacct tcgatgtgtc tcttctcacc attgacaatg gtgtcttcga agttgtggcc 961 actaatggag atactcatct gggtggagaa gactttgacc agcgtgtcat ggaacacttc 1021 atcaaactgt acaaaaagaa gacgggcaaa gatgtcagga aggacaatag agctgtgcag 1081 aaactccggc gcgaggtaga aaaggccaag gccctgtctt ctcagcatca agcaagaatt 1141 gaaattgagt ccttctatga aggagaagac ttttctgaga ccctgactcg ggccaaattt 1201 gaagagctca acatggatct gttccggtct actatgaagc ccgtccagaa agtgttggaa 1261 gattctgatt tgaagaagtc tgatattgat gaaattgttc ttgttggtgg ctcgactcga

FIG. 2

1321 attccaaaga ttcagcaact ggttaaagag ttcttcaatg gcaaggaacc atcccgtggc
1381 ataaacccag atgaagctgt agcgtatggt gctgctgtcc aggctggtgt gctctctggt
1441 gatcaagata caggtgacct ggtactgctt catgtatgtc cccttacact tggtattgaa
1501 actgtaggag gtgtcatgac caaactgatt ccaagtaata cagtggtgcc taccaagaac
1561 tctcagatct tttctacagc ttctgataat caaccaactg ttacaatcaa ggtctatgaa
1621 ggtgaaagac ccctgacaaa agacaatcat cttctgggta catttgatct gactggaatt
1681 cctcctgctc ctcgtggggt cccacagatt gaagtcacct ttgagataga tgtgaatggt
1741 attcttcgag tgacagctga agacaagggt acagggaaca aaaataagat cacaatcacc
1801 aatgaccaga atcgcctgac acctgaagaa atcgaaagga tggttaatga tgctgagaag
1861 tttgctgagg aagacaaaaa gctcaaggag cgcattgata ctagaaatga gttggaaagc
1921 tatgcctatt ctctaaagaa tcagattgga gataaagaaa agctgggagg taaactttcc
1981 tctgaagata aggagaccat ggaaaaagct gtagaagaaa agattgaatg gctggaaagc
2041 caccaagatg ctgacattga agacttcaaa gctaagaaga aggaactgga agaaattgtt
2101 caaccaatta tcagcaaact ctatggaagt gcaggccctc ccccaactgg tgaagaggat
2161 acagcagaaa aagatgagtt gtagacactg atctgctagt gctgtaatat tgtaaatact
2221 ggactcagga acttttgtta ggaaaaaatt gaaagaactt aagtctcgaa tgtaattgga
2281 atcttcacct cagagtggag ttgaactgct atagcctaag cggctgttta ctgcttttca
2341 ttagcagttg ctcacatgtc tttgggtggg gggggagaag aagaattggc catcttaaaa
2401 agcgggtaaa aaacctgggt tagggtgtgt gttcaccttc aaaatgttct atttaacaac
2461 tgggtcatgt gcatctggtg taggaagttt tttctaccat aagtgacacc aataaatgtt
2521 tgttatttac actggtcaaa aaaaaaaaaa aaaa

SEQ ID NO: 6

FIG. 2 (Continued)

His-tagged BiP analogue expressed by plasmid pQE2

10 20 30 40 50 60
MKHHHHHHHM RAEEEDKKED VGTVVGIDLG TTYSCVGVFK NGRVEIIAND QGNRITPSYV 70 80 90 100 110 120
AFTPEGERLI GDAAKNQLTS NPENTVFDAK RLIGRTWNDP SVQQDIKFLP FKVVEKKTKP 130 140 150 160 170 180
YIQVDIGGGQ TKTFAPEEIS AMVLTKMKET AEAYLGKKVT HAVVTVPAYF NDAQRQATKD 190 200 210 220 230 240
AGTIAGLNVM RIINEPTAAA IAYGLDKREG EKNILVFDLG GGTFDVSLLT IDNGVFEVVA 250 260 270 280 290 300
TNGDTHLGGE DFDQRVMEHF IKLYKKKTGK DVRKDNRAVQ KLRREVEKAK RALSSQHQAR 310 320 330 340 350 360
IEIESFYEGE DFSETLTRAK FEELNMDLFR STMKPVQKVL EDSDLKKSDI DEIVLVGGST 370 380 390 400 410 420
RIPKIQQLVK EFFNGKEPSR GINPDEAVAY GAAVQAGVLS GDQDTGDLVL LDVCPLTLGI 430 440 450 460 470 480
ETVGGVMTKL IPRNTVVPTK KSQIFSTASD NQPTVTIKVY EGERPLTKDN HLLGTFDLTG 490 500 510 520 530 540
IPPAPRGVPQ IEVTFEIDVN GILRVTAEDK GTGNKNKITI TNDQNRLTPE EIERMVNDAE 550 560 570 580 590 600
KFAEEDKKLK ERIDTRNELE SYAYSLKNQI GDKEKLGGKL SSEDKETMEK AVEEKIEWLE 610 620 630 640
SHQDADIEDF KAKKKELEEI VQPIISKLYG SAGPPPTGEE DTAEKDEL

SEQ ID NO: 4

FIG. 3

RAEEEDKKED VGTVVGIDLG TTYSCVGVFK NGRVEIIAND QGNRITPSYV

AFTPEGERLI GDAAKNQLTS NPENTVFDAK RLIGRTWNDP SVQQDIKFLP FKVVEKKTKP

YIQVDIGGGQ TKTFAPEEIS AMVLTKMKET AEAYLGKKVT HAVVTVPAYF NDAQRQATKD

AGTIAGLNVM RIINEPTAAA IAYGLDKREG EKNILVFDLG GGTFDVSLLT IDNGVFEVVA

TNGDTHLGGE DFDQRVMEHF IKLYKKKTGK DVRKDNRAVQ KLRREVEKAK RALSSQHQAR

IEIESFYEGE DFSETLTRAK FEELNMDLFR STMKPVQKVL EDSDLKKSDI DEIVLVGGST

RIPKIQQLVK EFFNGKEPSR GINPDEAVAY GAAVQAGVLS GDQDTGDLVL LDVCPLTLGI

ETVGGVMTKL IPRNTVVPTK KSQIFSTASD NQPTVTIKVY EGERPLTKDN HLLGTFDLTG

IPPAPRGVPQ IEVTFEIDVN GILRVTAEDK GTGNKNKITI TNDQNRLTPE EIERMVNDAE

KFAEEDKKLK ERIDTRNELE SYAYSLKNQI GDKEKLGGKL SSEDKETMEK AVEEKIEWLE

SHQDADIEDF KAKKKELEEI VQPIISKLYG SAGPPPTGEE DTAEKDEL

SEQ ID NO: 3

FIG. 4

SEQ ID NO: 8 attgtgagcggataacaatttcacacagaattcattaaagaggagaaattaactatgaaa
catcaccatcaccatcaccatatgcgggccgaggaggaggacaagaaggaggacgtgggc
acggtggtcggcatcgacctggggaccacctactcctgcgtcggcgtgttcaagaacggc
cgcgtggagatcatcgccaacgatcagggcaaccgcatcacgccgtcctatgtcgccttc
actcctgaaggggaacgtctgattggcgatgccgccaagaaccagctcacctccaacccc
gagaacacggtctttgacgccaagcggctcatcggccgcacgtggaatgacccgtctgtg
cagcaggacatcaagttcttgccgttcaaggtggttgaaaagaaaactaaaccatacatt
caagttgatattggaggtgggcaaacaaagacatttgctcctgaagaaatttctgccatg
gttctcactaaaatgaaagaaaccgctgaggcttatttgggaaagaaggttacccatgca
gttgttactgtaccagcctattttaatgatgcccaacgccaagcaaccaaagacgctgga
actattgctggcctaaatgttatgaggatcatcaacgagcctacggcagctgctattgct
tatggcctggataagagggaggggagaagaacatcctggtgtttgacctgggtggcgga
accttcgatgtgtctcttctcaccattgacaatggtgtcttcgaagttgtggccactaat
ggagatactcatctgggtggagaagactttgaccagcgtgtcatggaacacttcatcaaa
ctgtacaaaaagaagacgggcaaagatgtcaggaaagacaatagagctgtgcagaaactc
cggcgcgaggtagaaaaggccaaacgggccctgtcttctcagcatcaagcaagaattgaa
attgagtccttctatgaaggagaagacttttctgagaccctgactcgggccaaatttgaa
gagctcaacatggatctgttccggtctactatgaagcccgtccagaaagtgttggaagat
tctgatttgaagaagtctgatattgatgaaattgttcttgttggtggctcgactcgaatt
ccaaagattcagcaactggttaaagagttcttcaatggcaaggaaccatcccgtggcata
aacccagatgaagctgtagcgtatggtgctgctgtccaggctggtgtgctctctggtgat
caagatacaggtgacctggtactgcttgatgtatgtccccttacacttggtattgaaact
gtgggaggtgtcatgaccaaactgattccaaggaacacagtggtgcctaccaagaagtct
cagatcttttctacagcttctgataatcaaccaactgttacaatcaaggtctatgaaggt
gaaagacccctgacaaaagacaatcatcttctgggtacatttgatctgactggaattcct
cctgctcctcgtggggtcccacagattgaagtcacctttgagatagatgtgaatggtatt
cttcgagtgacagctgaagacaagggtacagggaacaaaaataagatcacaatcaccaat
gaccagaatcgcctgacacctgaagaaatcgaaaggatggttaatgatgctgagaagttt
gctgaggaagacaaaaagctcaaggagcgcattgatactagaaatgagttggaaagctat
gcctattctctaaagaatcagattggagataaagaaaagctgggaggtaaactttcctct
gaagataaggagaccatggaaaaagctgtagaagaaaagattgaatggctggaaagccac
caagatgctgacattgaagacttcaaagctaagaagaaggaactggaagaaattgttcaa
ccaattatcagcaaactctatggaagtgcaggccctcccccaactggtgaagaggataca
gcagaaaaagatgagttgtaggcggccgcgggtacccacgtgtcgacctgcagccaagct

FIG. 5B

```
  1 ......MKHHHHHHHMRAEEEDKKEDVGTVVGIDLGTTYSCVGVFKNGRV  44
                    ||||||||||||||||||||||||||||||||||
  1 MKLSLVAAMLLLLSAARAEEEDKKEDVGTVVGIDLGTTYSCVGVFKNGRV  50
              .         .         .         .         .
 45 EIIANDQGNRITPSYVAFTPEGERLIGDAAKNQLTSNPENTVFDAKRLIG  94
    ||||||||||||||||||||||||||||||||||||||||||||||||||
 51 EIIANDQGNRITPSYVAFTPEGERLIGDAAKNQLTSNPENTVFDAKRLIG 100
              .         .         .         .         .
 95 RTWNDPSVQQDIKFLPFKVVEKKTKPYIQVDIGGGQTKTFAPEEISAMVL 144
    ||||||||||||||||||||||||||||||||||||||||||||||||||
101 RTWNDPSVQQDIKFLPFKVVEKKTKPYIQVDIGGGQTKTFAPEEISAMVL 150
              .         .         .         .         .
145 TKMKETAEAYLGKKVTHAVVTVPAYFNDAQRQATKDAGTIAGLNVMRIIN 194
    ||||||||||||||||||||||||||||||||||||||||||||||||||
151 TKMKETAEAYLGKKVTHAVVTVPAYFNDAQRQATKDAGTIAGLNVMRIIN 200
              .         .         .         .         .
195 EPTAAAIAYGLDKREGEKNILVFDLGGGTFDVSLLTIDNGVFEVVATNGD 244
    ||||||||||||||||||||||||||||||||||||||||||||||||||
201 EPTAAAIAYGLDKREGEKNILVFDLGGGTFDVSLLTIDNGVFEVVATNGD 250
              .         .         .         .         .
245 THLGGEDFDQRVMEHFIKLYKKKTGKDVRKDNRAVQKLRREVEKAKRALS 294
    ||||||||||||||||||||||||||||||||||||||||||||||||||
251 THLGGEDFDQRVMEHFIKLYKKKTGKDVRKDNRAVQKLRREVEKAKRALS 300
              .         .         .         .         .
295 SQHQARIEIESFYEGEDFSETLTRAKFEELNMDLFRSTMKPVQKVLEDSD 344
    ||||||||||||||||||||||||||||||||||||||||||||||||||
301 SQHQARIEIESFYEGEDFSETLTRAKFEELNMDLFRSTMKPVQKVLEDSD 350
              .         .         .         .         .
```

FIG. 6

```
345 LKKSDIDEIVLVGGSTRIPKIQQLVKEFFNGKEPSRGINPDEAVAYGAAV 394
    ||||||||||||||||||||||||||||||||||||||||||||||||||
351 LKKSDIDEIVLVGGSTRIPKIQQLVKEFFNGKEPSRGINPDEAVAYGAAV 400
              .         .         .         .         .
395 QAGVLSGDQDTGDLVLLDVCPLTLGIETVGGVMTKLIPRNTVVPTKKSQI 444
    ||||||||||||||||||||||||||||||||||||||||||||||||||
401 QAGVLSGDQDTGDLVLLDVCPLTLGIETVGGVMTKLIPRNTVVPTKKSQI 450
              .         .         .         .         .
445 FSTASDNQPTVTIKVYEGERPLTKDNHLLGTFDLTGIPPAPRGVPQIEVT 494
    ||||||||||||||||||||||||||||||||||||||||||||||||||
451 FSTASDNQPTVTIKVYEGERPLTKDNHLLGTFDLTGIPPAPRGVPQIEVT 500
              .         .         .         .         .
495 FEIDVNGILRVTAEDKGTGNKNKITITNDQNRLTPEEIERMVNDAEKFAE 544
    ||||||||||||||||||||||||||||||||||||||||||||||||||
501 FEIDVNGILRVTAEDKGTGNKNKITITNDQNRLTPEEIERMVNDAEKFAE 550
              .         .         .         .         .
545 EDKKLKERIDTRNELESYAYSLKNQIGDKEKLGGKLSSEDKETMEKAVEE 594
    ||||||||||||||||||||||||||||||||||||||||||||||||||
551 EDKKLKERIDTRNELESYAYSLKNQIGDKEKLGGKLSSEDKETMEKAVEE 600
              .         .         .         .         .
595 KIEWLESHQDADIEDFKAKKKELEEIVQPIISKLYGSAGPPPTGEEDTAE 644
    ||||||||||||||||||||||||||||||||||||||||||||||||||
601 KIEWLESHQDADIEDFKAKKKELEEIVQPIISKLYGSAGPPPTGEEDTAE 650

645 KDEL* 649 (SEQ ID NO: 4)
    |||||
651 KDEL* 655 (SEQ ID NO: 5)
```

FIG. 6 (Continued)

```
<400> SEQUENCE: 1

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320
```

FIG. 7

Met Lys Pro Val Gln Lys Val Leu Glu Asp Ser Asp Leu Lys Lys Ser
325 330 335

Asp Ile Asp Glu Ile Val Leu Val Gly Gly Ser Thr Arg Ile Pro Lys
340 345 350

Ile Gln Gln Leu Val Lys Glu Phe Phe Asn Gly Lys Glu Pro Ser Arg
355 360 365

Gly Ile Asn Pro Asp Glu Ala Val Ala Tyr Gly Ala Ala Val Gln Ala
370 375 380

Gly Val Leu Ser Gly Asp Gln Asp Thr Gly Asp Leu Val Leu Leu Asp
385 390 395 400

Val Cys Pro Leu Thr Leu Gly Ile Glu Thr Val Gly Gly Val Met Thr
405 410 415

Lys Leu Ile Pro Arg Asn Thr Val Val Pro Thr Lys Lys Ser Gln Ile
420 425 430

Phe Ser Thr Ala Ser Asp Asn Gln Pro Thr Val Thr Ile Lys Val Tyr
435 440 445

Glu Gly Glu Arg Pro Leu Thr Lys Asp Asn His Leu Leu Gly Thr Phe
450 455 460

Asp Leu Thr Gly Ile Pro Pro Ala Pro Arg Gly Val Pro Gln Ile Glu
465 470 475 480

Val Thr Phe Glu Ile Asp Val Asn Gly Ile Leu Arg Val Thr Ala Glu
485 490 495

Asp Lys Gly Thr Gly Asn Lys Asn Lys Ile Thr Ile Thr Asn Asp Gln
500 505 510

Asn Arg Leu Thr Pro Glu Glu Ile Glu Arg Met Val Asn Asp Ala Glu
515 520 525

Lys Phe Ala Glu Glu Asp Lys Lys Leu Lys Glu Arg Ile Asp Thr Arg
530 535 540

Asn Glu Leu Glu Ser Tyr Ala Tyr Ser Leu Lys Asn Gln Ile Gly Asp
545 550 555 560

Lys Glu Lys Leu Gly Gly Lys Leu Ser Ser Glu Asp Lys Glu Thr Met
565 570 575

Glu Lys Ala Val Glu Glu Lys Ile Glu Trp Leu Glu Ser His Gln Asp
580 585 590

Ala Asp Ile Glu Asp Phe Lys Ala Lys Lys Lys Glu Leu Glu Glu Ile
595 600 605

Val Gln Pro Ile Ile Ser Lys Leu Tyr Gly Ser Ala Gly Pro Pro Pro
610 615 620

Thr Gly Glu Glu Asp Thr Ala Glu Leu His His His His His His
625 630 635

FIG. 7 (Continued)

```
<400> SEQUENCE: 2

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320
```

FIG. 8

```
Met Lys Pro Val Gln Lys Val Leu Glu Asp Ser Asp Leu Lys Lys Ser
                325                 330                 335
Asp Ile Asp Glu Ile Val Leu Val Gly Gly Ser Thr Arg Ile Pro Lys
            340                 345                 350
Ile Gln Gln Leu Val Lys Glu Phe Phe Asn Gly Lys Glu Pro Ser Arg
        355                 360                 365
Gly Ile Asn Pro Asp Glu Ala Val Ala Tyr Gly Ala Ala Val Gln Ala
    370                 375                 380
Gly Val Leu Ser Gly Asp Gln Asp Thr Gly Asp Leu Val Leu Leu Asp
385                 390                 395                 400
Val Cys Pro Leu Thr Leu Gly Ile Glu Thr Val Gly Gly Val Met Thr
                405                 410                 415
Lys Leu Ile Pro Arg Asn Thr Val Val Pro Thr Lys Lys Ser Gln Ile
            420                 425                 430
Phe Ser Thr Ala Ser Asp Asn Gln Pro Thr Val Thr Ile Lys Val Tyr
        435                 440                 445
Glu Gly Glu Arg Pro Leu Thr Lys Asp Asn His Leu Leu Gly Thr Phe
    450                 455                 460
Asp Leu Thr Gly Ile Pro Pro Ala Pro Arg Gly Val Pro Gln Ile Glu
465                 470                 475                 480
Val Thr Phe Glu Ile Asp Val Asn Gly Ile Leu Arg Val Thr Ala Glu
                485                 490                 495
Asp Lys Gly Thr Gly Asn Lys Asn Lys Ile Thr Ile Thr Asn Asp Gln
            500                 505                 510
Asn Arg Leu Thr Pro Glu Glu Ile Glu Arg Met Val Asn Asp Ala Glu
        515                 520                 525
Lys Phe Ala Glu Glu Asp Lys Lys Leu Lys Glu Arg Ile Asp Thr Arg
    530                 535                 540
Asn Glu Leu Glu Ser Tyr Ala Tyr Ser Leu Lys Asn Gln Ile Gly Asp
545                 550                 555                 560
Lys Glu Lys Leu Gly Gly Lys Leu Ser Ser Glu Asp Lys Glu Thr Met
                565                 570                 575
Glu Lys Ala Val Glu Glu Lys Ile Glu Trp Leu Glu Ser His Gln Asp
            580                 585                 590
Ala Asp Ile Glu Asp Phe Lys Ala Lys Lys Lys Glu Leu Glu Glu Ile
        595                 600                 605
Val Gln Pro Ile Ile Ser Lys Leu Tyr Gly Ser Ala Gly Pro Pro Pro
    610                 615                 620
Thr Gly Glu Glu Asp Thr Ala Glu Leu
625                 630
```

FIG. 8 (Continued)

MEEDKKED VGTVVGIDLG TTYSCVGVFK NGRVEIIAND QGNRITPSYV

AFTPEGERLI GDAAKNQLTS NPENTVFDAK RLIGRTWNDP SVQQDIKFLP FKVVEKKTKP

YIQVDIGGGQ TKTFAPEEIS AMVLTKMKET AEAYLGKKVT HAVVTVPAYF NDAQRQATKD

AGTIAGLNVM RIINEPTAAA IAYGLDKREG EKNILVFDLG GGTFDVSLLT IDNGVFEVVA

TNGDTHLGGE DFDQRVMEHF IKLYKKKTGK DVRKDNRAVQ KLRREVEKAK RALSSQHQAR

IEIESFYEGE DFSETLTRAK FEELNMDLFR STMKPVQKVL EDSDLKKSDI DEIVLVGGST

RIPKIQQLVK EFFNGKEPSR GINPDEAVAY GAAVQAGVLS GDQDTGDLVL LDVCPLTLGI

ETVGGVMTKL IPRNTVVPTK KSQIFSTASD NQPTVTIKVY EGERPLTKDN HLLGTFDLTG

IPPAPRGVPQ IEVTFEIDVN GILRVTAEDK GTGNKNKITI TNDQNRLTPE EIERMVNDAE

KFAEEDKKLK ERIDTRNELE SYAYSLKNQI GDKEKLGGKL SSEDKETMEK AVEEKIEWLE

SHQDADIEDF KAKKKELEEI VQPIISKLYG SAGPPPTGEE DTAEKDEL

SEQ ID NO: 7

FIG. 9

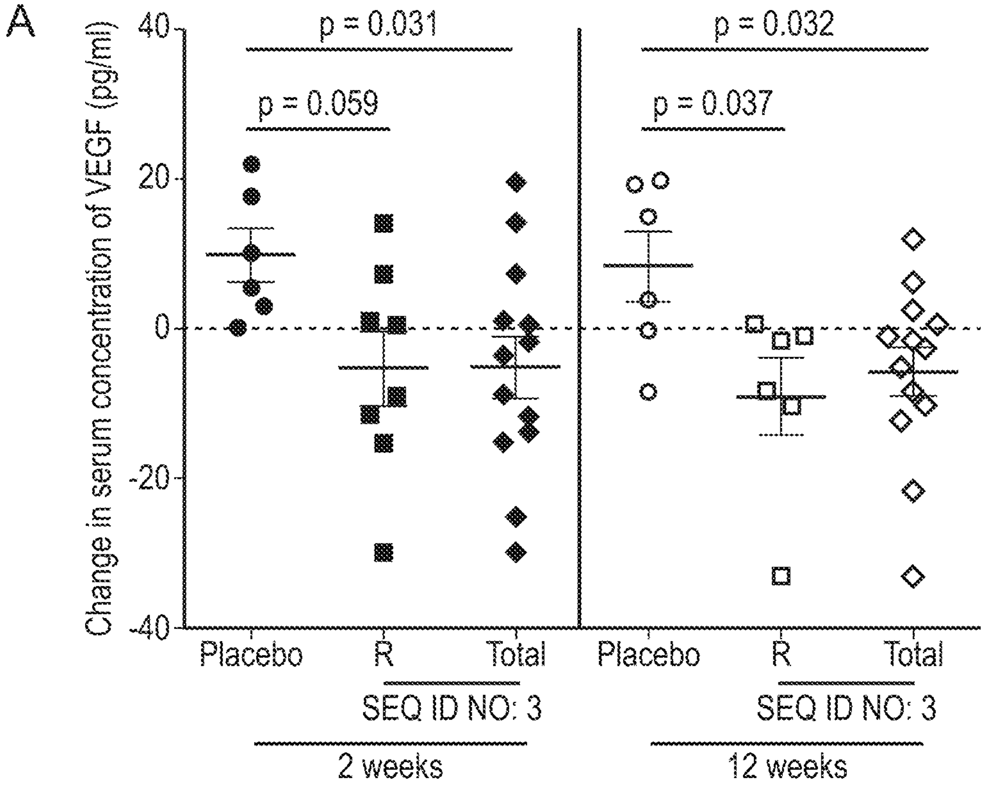
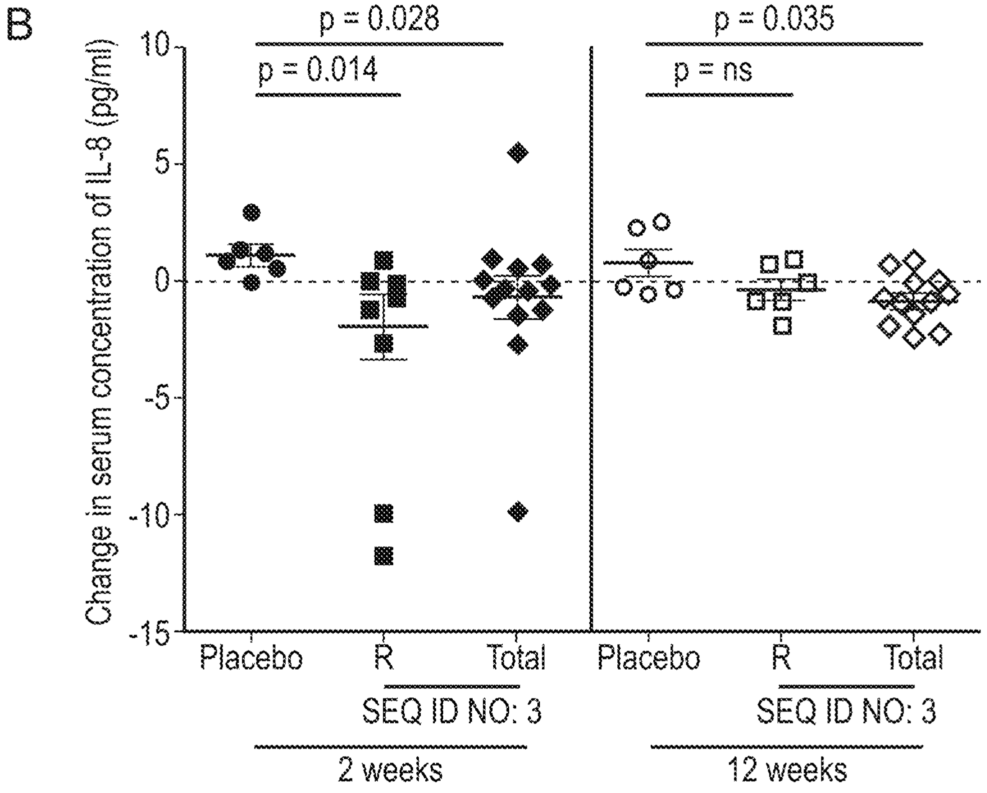
FIG. 13

SEQUENCE LISTING

```
<160> NUMBER OF SEQ ID NOS: 14

<210> SEQ ID NO 1
<211> LENGTH: 639
<212> TYPE: PRT
<213> ORGANISM: Artificial Sequence
<220> FEATURE:
<223> OTHER INFORMATION: Binding Immunoglobulin Protein (BiP) analogue

<400> SEQUENCE: 1

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
```

```
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
        355                 360                 365

Gly Ile Asn Pro Asp Glu Ala Val Ala Tyr Gly Ala Ala Val Gln Ala
    370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
                405                 410                 415

Lys Leu Ile Pro Arg Asn Thr Val Val Pro Thr Lys Lys Ser Gln Ile
            420                 425                 430

Phe Ser Thr Ala Ser Asp Asn Gln Pro Thr Val Thr Ile Lys Val Tyr
        435                 440                 445

Glu Gly Glu Arg Pro Leu Thr Lys Asp Asn His Leu Leu Gly Thr Phe
    450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu
        515                 520                 525

Lys Phe Ala Glu Glu Asp Lys Lys Leu Lys Glu Arg Ile Asp Thr Arg
    530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Lys Glu Leu Glu Glu Ile
        595                 600                 605

Val Gln Pro Ile Ile Ser Lys Leu Tyr Gly Ser Ala Gly Pro Pro Pro
    610                 615                 620

Thr Gly Glu Glu Asp Thr Ala Glu Leu His His His His His His
625                 630                 635
```

<210> SEQ ID NO 2
<211> LENGTH: 633
<212> TYPE: PRT
<213> ORGANISM: Artificial Sequence
<220> FEATURE:
<223> OTHER INFORMATION: BiP analogue

<400> SEQUENCE: 2

```
Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
```

```
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
        355                 360                 365

Gly Ile Asn Pro Asp Glu Ala Val Ala Tyr Gly Ala Ala Val Gln Ala
    370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
                405                 410                 415

Lys Leu Ile Pro Arg Asn Thr Val Val Pro Thr Lys Lys Ser Gln Ile
            420                 425                 430

Phe Ser Thr Ala Ser Asp Asn Gln Pro Thr Val Thr Ile Lys Val Tyr
        435                 440                 445

Glu Gly Glu Arg Pro Leu Thr Lys Asp Asn His Leu Leu Gly Thr Phe
    450                 455                 460

Asp Leu Thr Gly Ile Pro Pro Ala Pro Arg Gly Val Pro Gln Ile Glu
465                 470                 475                 480
```

```
Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu
        515                 520                 525

Lys Phe Ala Glu Glu Asp Lys Lys Leu Lys Glu Arg Ile Asp Thr Arg
    530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Lys Glu Leu Glu Glu Ile
        595                 600                 605

Val Gln Pro Ile Ile Ser Lys Leu Tyr Gly Ser Ala Gly Pro Pro Pro
    610                 615                 620

Thr Gly Glu Glu Asp Thr Ala Glu Leu
625                 630
```

<210> SEQ ID NO 3
<211> LENGTH: 638
<212> TYPE: PRT
<213> ORGANISM: Artificial Sequence
<220> FEATURE:
<223> OTHER INFORMATION: BiP analogue

<400> SEQUENCE: 3

```
Arg Ala Glu Glu Glu Asp Lys Lys Glu Asp Val Gly Thr Val Val Gly
1               5                   10                  15

Ile Asp Leu Gly Thr Thr Tyr Ser Cys Val Gly Val Phe Lys Asn Gly
            20                  25                  30

Arg Val Glu Ile Ile Ala Asn Asp Gln Gly Asn Arg Ile Thr Pro Ser
        35                  40                  45

Tyr Val Ala Phe Thr Pro Glu Gly Glu Arg Leu Ile Gly Asp Ala Ala
    50                  55                  60

Lys Asn Gln Leu Thr Ser Asn Pro Glu Asn Thr Val Phe Asp Ala Lys
65                  70                  75                  80

Arg Leu Ile Gly Arg Thr Trp Asn Asp Pro Ser Val Gln Gln Asp Ile
                85                  90                  95

Lys Phe Leu Pro Phe Lys Val Val Glu Lys Lys Thr Lys Pro Tyr Ile
            100                 105                 110

Gln Val Asp Ile Gly Gly Gly Gln Thr Lys Thr Phe Ala Pro Glu Glu
        115                 120                 125

Ile Ser Ala Met Val Leu Thr Lys Met Lys Glu Thr Ala Glu Ala Tyr
    130                 135                 140

Leu Gly Lys Lys Val Thr His Ala Val Val Thr Val Pro Ala Tyr Phe
145                 150                 155                 160

Asn Asp Ala Gln Arg Gln Ala Thr Lys Asp Ala Gly Thr Ile Ala Gly
                165                 170                 175

Leu Asn Val Met Arg Ile Ile Asn Glu Pro Thr Ala Ala Ala Ile Ala
            180                 185                 190

Tyr Gly Leu Asp Lys Arg Glu Gly Glu Lys Asn Ile Leu Val Phe Asp
        195                 200                 205
```

-continued

```
Leu Gly Gly Gly Thr Phe Asp Val Ser Leu Leu Thr Ile Asp Asn Gly
    210                 215                 220

Val Phe Glu Val Val Ala Thr Asn Gly Asp Thr His Leu Gly Gly Glu
225                 230                 235                 240

Asp Phe Asp Gln Arg Val Met Glu His Phe Ile Lys Leu Tyr Lys Lys
                245                 250                 255

Lys Thr Gly Lys Asp Val Arg Lys Asp Asn Arg Ala Val Gln Lys Leu
            260                 265                 270

Arg Arg Glu Val Glu Lys Ala Lys Arg Ala Leu Ser Ser Gln His Gln
        275                 280                 285

Ala Arg Ile Glu Ile Glu Ser Phe Tyr Glu Gly Glu Asp Phe Ser Glu
    290                 295                 300

Thr Leu Thr Arg Ala Lys Phe Glu Glu Leu Asn Met Asp Leu Phe Arg
305                 310                 315                 320

Ser Thr Met Lys Pro Val Gln Lys Val Leu Glu Asp Ser Asp Leu Lys
                325                 330                 335

Lys Ser Asp Ile Asp Glu Ile Val Leu Val Gly Gly Ser Thr Arg Ile
            340                 345                 350

Pro Lys Ile Gln Gln Leu Val Lys Glu Phe Phe Asn Gly Lys Glu Pro
        355                 360                 365

Ser Arg Gly Ile Asn Pro Asp Glu Ala Val Ala Tyr Gly Ala Ala Val
    370                 375                 380

Gln Ala Gly Val Leu Ser Gly Asp Gln Asp Thr Gly Asp Leu Val Leu
385                 390                 395                 400

Leu Asp Val Cys Pro Leu Thr Leu Gly Ile Glu Thr Val Gly Gly Val
                405                 410                 415

Met Thr Lys Leu Ile Pro Arg Asn Thr Val Val Pro Thr Lys Lys Ser
            420                 425                 430

Gln Ile Phe Ser Thr Ala Ser Asp Asn Gln Pro Thr Val Thr Ile Lys
        435                 440                 445

Val Tyr Glu Gly Glu Arg Pro Leu Thr Lys Asp Asn His Leu Leu Gly
    450                 455                 460

Thr Phe Asp Leu Thr Gly Ile Pro Pro Ala Pro Arg Gly Val Pro Gln
465                 470                 475                 480

Ile Glu Val Thr Phe Glu Ile Asp Val Asn Gly Ile Leu Arg Val Thr
                485                 490                 495

Ala Glu Asp Lys Gly Thr Gly Asn Lys Asn Lys Ile Thr Ile Thr Asn
            500                 505                 510

Asp Gln Asn Arg Leu Thr Pro Glu Glu Ile Glu Arg Met Val Asn Asp
        515                 520                 525

Ala Glu Lys Phe Ala Glu Glu Asp Lys Lys Leu Lys Glu Arg Ile Asp
    530                 535                 540

Thr Arg Asn Glu Leu Glu Ser Tyr Ala Tyr Ser Leu Lys Asn Gln Ile
545                 550                 555                 560

Gly Asp Lys Glu Lys Leu Gly Gly Lys Leu Ser Ser Glu Asp Lys Glu
                565                 570                 575

Thr Met Glu Lys Ala Val Glu Glu Lys Ile Glu Trp Leu Glu Ser His
            580                 585                 590

Gln Asp Ala Asp Ile Glu Asp Phe Lys Ala Lys Lys Lys Glu Leu Glu
        595                 600                 605

Glu Ile Val Gln Pro Ile Ile Ser Lys Leu Tyr Gly Ser Ala Gly Pro
    610                 615                 620
```

```
Pro Pro Thr Gly Glu Glu Asp Thr Ala Glu Lys Asp Glu Leu
625                 630                 635


<210> SEQ ID NO 4
<211> LENGTH: 648
<212> TYPE: PRT
<213> ORGANISM: Artificial Sequence
<220> FEATURE:
<223> OTHER INFORMATION: His-tagged BiP analogue expressed by plasmid
      pQE2

<400> SEQUENCE: 4

Met Lys His His His His His His His Met Arg Ala Glu Glu Glu Asp
1               5                   10                  15

Lys Lys Glu Asp Val Gly Thr Val Val Gly Ile Asp Leu Gly Thr Thr
            20                  25                  30

Tyr Ser Cys Val Gly Val Phe Lys Asn Gly Arg Val Glu Ile Ile Ala
        35                  40                  45

Asn Asp Gln Gly Asn Arg Ile Thr Pro Ser Tyr Val Ala Phe Thr Pro
    50                  55                  60

Glu Gly Glu Arg Leu Ile Gly Asp Ala Ala Lys Asn Gln Leu Thr Ser
65                  70                  75                  80

Asn Pro Glu Asn Thr Val Phe Asp Ala Lys Arg Leu Ile Gly Arg Thr
                85                  90                  95

Trp Asn Asp Pro Ser Val Gln Gln Asp Ile Lys Phe Leu Pro Phe Lys
            100                 105                 110

Val Val Glu Lys Lys Thr Lys Pro Tyr Ile Gln Val Asp Ile Gly Gly
        115                 120                 125

Gly Gln Thr Lys Thr Phe Ala Pro Glu Glu Ile Ser Ala Met Val Leu
    130                 135                 140

Thr Lys Met Lys Glu Thr Ala Glu Ala Tyr Leu Gly Lys Lys Val Thr
145                 150                 155                 160

His Ala Val Val Thr Val Pro Ala Tyr Phe Asn Asp Ala Gln Arg Gln
                165                 170                 175

Ala Thr Lys Asp Ala Gly Thr Ile Ala Gly Leu Asn Val Met Arg Ile
            180                 185                 190

Ile Asn Glu Pro Thr Ala Ala Ala Ile Ala Tyr Gly Leu Asp Lys Arg
        195                 200                 205

Glu Gly Glu Lys Asn Ile Leu Val Phe Asp Leu Gly Gly Gly Thr Phe
    210                 215                 220

Asp Val Ser Leu Leu Thr Ile Asp Asn Gly Val Phe Glu Val Val Ala
225                 230                 235                 240

Thr Asn Gly Asp Thr His Leu Gly Gly Glu Asp Phe Asp Gln Arg Val
                245                 250                 255

Met Glu His Phe Ile Lys Leu Tyr Lys Lys Lys Thr Gly Lys Asp Val
            260                 265                 270

Arg Lys Asp Asn Arg Ala Val Gln Lys Leu Arg Arg Glu Val Glu Lys
        275                 280                 285

Ala Lys Arg Ala Leu Ser Ser Gln His Gln Ala Arg Ile Glu Ile Glu
    290                 295                 300

Ser Phe Tyr Glu Gly Glu Asp Phe Ser Glu Thr Leu Thr Arg Ala Lys
305                 310                 315                 320

Phe Glu Glu Leu Asn Met Asp Leu Phe Arg Ser Thr Met Lys Pro Val
                325                 330                 335

Gln Lys Val Leu Glu Asp Ser Asp Leu Lys Lys Ser Asp Ile Asp Glu
            340                 345                 350
```

Ile Val Leu Val Gly Gly Ser Thr Arg Ile Pro Lys Ile Gln Gln Leu
355 360 365

Val Lys Glu Phe Phe Asn Gly Lys Glu Pro Ser Arg Gly Ile Asn Pro
370 375 380

Asp Glu Ala Val Ala Tyr Gly Ala Ala Val Gln Ala Gly Val Leu Ser
385 390 395 400

Gly Asp Gln Asp Thr Gly Asp Leu Val Leu Leu Asp Val Cys Pro Leu
405 410 415

Thr Leu Gly Ile Glu Thr Val Gly Gly Val Met Thr Lys Leu Ile Pro
420 425 430

Arg Asn Thr Val Val Pro Thr Lys Lys Ser Gln Ile Phe Ser Thr Ala
435 440 445

Ser Asp Asn Gln Pro Thr Val Thr Ile Lys Val Tyr Glu Gly Glu Arg
450 455 460

Pro Leu Thr Lys Asp Asn His Leu Leu Gly Thr Phe Asp Leu Thr Gly
465 470 475 480

Ile Pro Pro Ala Pro Arg Gly Val Pro Gln Ile Glu Val Thr Phe Glu
485 490 495

Ile Asp Val Asn Gly Ile Leu Arg Val Thr Ala Glu Asp Lys Gly Thr
500 505 510

Gly Asn Lys Asn Lys Ile Thr Ile Thr Asn Asp Gln Asn Arg Leu Thr
515 520 525

Pro Glu Glu Ile Glu Arg Met Val Asn Asp Ala Glu Lys Phe Ala Glu
530 535 540

Glu Asp Lys Lys Leu Lys Glu Arg Ile Asp Thr Arg Asn Glu Leu Glu
545 550 555 560

Ser Tyr Ala Tyr Ser Leu Lys Asn Gln Ile Gly Asp Lys Glu Lys Leu
565 570 575

Gly Gly Lys Leu Ser Ser Glu Asp Lys Glu Thr Met Glu Lys Ala Val
580 585 590

Glu Glu Lys Ile Glu Trp Leu Glu Ser His Gln Asp Ala Asp Ile Glu
595 600 605

Asp Phe Lys Ala Lys Lys Lys Glu Leu Glu Glu Ile Val Gln Pro Ile
610 615 620

Ile Ser Lys Leu Tyr Gly Ser Ala Gly Pro Pro Pro Thr Gly Glu Glu
625 630 635 640

Asp Thr Ala Glu Lys Asp Glu Leu
645

<210> SEQ ID NO 5
<211> LENGTH: 654
<212> TYPE: PRT
<213> ORGANISM: Homo sapiens

<400> SEQUENCE: 5

Met Lys Leu Ser Leu Val Ala Ala Met Leu Leu Leu Leu Ser Ala Ala
1 5 10 15

Arg Ala Glu Glu Glu Asp Lys Lys Glu Asp Val Gly Thr Val Val Gly
20 25 30

Ile Asp Leu Gly Thr Thr Tyr Ser Cys Val Gly Val Phe Lys Asn Gly
35 40 45

Arg Val Glu Ile Ile Ala Asn Asp Gln Gly Asn Arg Ile Thr Pro Ser
50 55 60

Tyr Val Ala Phe Thr Pro Glu Gly Glu Arg Leu Ile Gly Asp Ala Ala

-continued

```
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495
```

```
Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650
```

<210> SEQ ID NO 6
<211> LENGTH: 2554
<212> TYPE: DNA
<213> ORGANISM: Homo sapiens

<400> SEQUENCE: 6

```
aggtcgacgc cggccaagac agcacagaca gattgaccta ttggggtgtt tcgcgagtgt     60

gagagggaag cgccgcggcc tgtatttcta gacctgccct tcgcctggtt cgtggcgcct    120

tgtgaccccg ggcccctgcc gcctgcaagt cggaaattgc gctgtgctcc tgtgctacgg    180

cctgtggctg gactgcctgc tgctgcccaa ctggctggca agatgaagct ctccctggtg    240

gccgcgatgc tgctgctgct cagcgcggcg cgggccgagg aggaggacaa gaaggaggac    300

gtgggcacgg tggtcggcat cgacttgggg accacctact cctgcgtcgg cgtgttcaag    360

aacggccgcg tggagatcat cgccaacgat cagggcaacc gcatcacgcc gtcctatgtc    420

gccttcactc ctgaagggga acgtctgatt ggcgatgccg ccaagaacca gctcacctcc    480

aaccccgaga acacggtctt tgacgccaag cggctcatcg gccgcacgtg gaatgacccg    540

tctgtgcagc aggacatcaa gttcttgccg ttcaaggtgg ttgaaaagaa aactaaacca    600

tacattcaag ttgatattgg aggtgggcaa acaaagacat ttgctcctga agaaatttct    660

gccatggttc tcactaaaat gaaagaaacc gctgaggctt atttgggaaa gaaggttacc    720

catgcagttg ttactgtacc agcctatttt aatgatgccc aacgccaagc aaccaaagac    780

gctggaacta ttgctggcct aaatgttatg aggatcatca acgagcctac ggcagctgct    840

attgcttatg gcctggataa gagggagggg gagaagaaca tcctggtgtt tgacctgggt    900

ggcggaacct tcgatgtgtc tcttctcacc attgacaatg gtgtcttcga agttgtggcc    960

actaatggag atactcatct gggtggagaa gactttgacc agcgtgtcat ggaacacttc   1020

atcaaactgt acaaaaagaa gacgggcaaa gatgtcagga aggacaatag agctgtgcag   1080

aaactccggc gcgaggtaga aaaggccaag gccctgtctt ctcagcatca agcaagaatt   1140

gaaattgagt ccttctatga aggagaagac ttttctgaga ccctgactcg ggccaaattt   1200
```

```
gaagagctca acatggatct gttccggtct actatgaagc ccgtccagaa agtgttggaa   1260

gattctgatt tgaagaagtc tgatattgat gaaattgttc ttgttggtgg ctcgactcga   1320

attccaaaga ttcagcaact ggttaaagag ttcttcaatg gcaaggaacc atcccgtggc   1380

ataaacccag atgaagctgt agcgtatggt gctgctgtcc aggctggtgt gctctctggt   1440

gatcaagata caggtgacct ggtactgctt catgtatgtc cccttacact tggtattgaa   1500

actgtaggag gtgtcatgac caaactgatt ccaagtaata cagtggtgcc taccaagaac   1560

tctcagatct tttctacagc ttctgataat caaccaactg ttacaatcaa ggtctatgaa   1620

ggtgaaagac ccctgacaaa agacaatcat cttctgggta catttgatct gactggaatt   1680

cctcctgctc ctcgtggggt cccacagatt gaagtcacct ttgagataga tgtgaatggt   1740

attcttcgag tgacagctga agacaagggt acagggaaca aaaataagat cacaatcacc   1800

aatgaccaga atcgcctgac acctgaagaa atcgaaagga tggttaatga tgctgagaag   1860

tttgctgagg aagacaaaaa gctcaaggag cgcattgata ctagaaatga gttggaaagc   1920

tatgcctatt ctctaaagaa tcagattgga gataaagaaa agctgggagg taaactttcc   1980

tctgaagata aggagaccat ggaaaaagct gtagaagaaa agattgaatg gctggaaagc   2040

caccaagatg ctgacattga agacttcaaa gctaagaaga aggaactgga agaaattgtt   2100

caaccaatta tcagcaaact ctatggaagt gcaggccctc ccccaactgg tgaagaggat   2160

acagcagaaa aagatgagtt gtagacactg atctgctagt gctgtaatat tgtaaatact   2220

ggactcagga acttttgtta ggaaaaaatt gaaagaactt aagtctcgaa tgtaattgga   2280

atcttcacct cagagtggag ttgaactgct atagcctaag cggctgttta ctgcttttca   2340

ttagcagttg ctcacatgtc tttgggtggg gggggagaag aagaattggc catcttaaaa   2400

agcgggtaaa aaacctgggt tagggtgtgt gttcaccttc aaaatgttct atttaacaac   2460

tgggtcatgt gcatctggtg taggaagttt tttctaccat aagtgacacc aataaatgtt   2520

tgttatttac actggtcaaa aaaaaaaaaa aaaa                               2554
```

```
<210> SEQ ID NO 7
<211> LENGTH: 636
<212> TYPE: PRT
<213> ORGANISM: Artificial Sequence
<220> FEATURE:
<223> OTHER INFORMATION: BiP analogue with the His-tag removed and KDEL
      sequence restored

<400> SEQUENCE: 7

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
```

-continued

```
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
        355                 360                 365

Gly Ile Asn Pro Asp Glu Ala Val Ala Tyr Gly Ala Ala Val Gln Ala
    370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
                405                 410                 415

Lys Leu Ile Pro Arg Asn Thr Val Val Pro Thr Lys Lys Ser Gln Ile
            420                 425                 430

Phe Ser Thr Ala Ser Asp Asn Gln Pro Thr Val Thr Ile Lys Val Tyr
        435                 440                 445

Glu Gly Glu Arg Pro Leu Thr Lys Asp Asn His Leu Leu Gly Thr Phe
    450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu
        515                 520                 525

Lys Phe Ala Glu Glu Asp Lys Lys Leu Lys Glu Arg Ile Asp Thr Arg
    530                 535                 540
```

```
Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Lys Glu Leu Glu Glu Ile
        595                 600                 605

Val Gln Pro Ile Ile Ser Lys Leu Tyr Gly Ser Ala Gly Pro Pro Pro
    610                 615                 620

Thr Gly Glu Glu Asp Thr Ala Glu Lys Asp Glu Leu
625                 630                 635


<210> SEQ ID NO 8
<211> LENGTH: 2040
<212> TYPE: DNA
<213> ORGANISM: Artificial Sequence
<220> FEATURE:
<223> OTHER INFORMATION: BiP Sequence cloned into NdeI/NotI site of
      vector pQE-2

<400> SEQUENCE: 8

attgtgagcg gataacaatt tcacacagaa ttcattaaag aggagaaatt aactatgaaa      60

catcaccatc accatcacca tatgcgggcc gaggaggagg acaagaagga ggacgtgggc     120

acggtggtcg gcatcgacct ggggaccacc tactcctgcg tcggcgtgtt caagaacggc     180

cgcgtggaga tcatcgccaa cgatcagggc aaccgcatca cgccgtccta tgtcgccttc     240

actcctgaag ggaacgtctc gattggcgat gccgccaaga accagctcac ctccaacccc     300

gagaacacgg tctttgacgc caagcggctc atcggccgca cgtggaatga cccgtctgtg     360

cagcaggaca tcaagttctt gccgttcaag gtggttgaaa agaaaactaa accatacatt     420

caagttgata ttggaggtgg gcaaacaaag acatttgctc ctgaagaaat ttctgccatg     480

gttctcacta aaatgaaaga aaccgctgag gcttatttgg gaaagaaggt tacccatgca     540

gttgttactg taccagccta ttttaatgat gcccaacgcc aagcaaccaa agacgctgga     600

actattgctg gcctaaatgt tatgaggatc atcaacgagc ctacggcagc tgctattgct     660

tatggcctgg ataagaggga gggggagaag aacatcctgg tgtttgacct gggtggcgga     720

accttcgatg tgtctcttct caccattgac aatggtgtct tcgaagttgt ggccactaat     780

ggagatactc atctgggtgg agaagacttt gaccagcgtg tcatggaaca cttcatcaaa     840

ctgtacaaaa agaagacggg caaagatgtc aggaaagaca atagagctgt gcagaaactc     900

cggcgcgagg tagaaaaggc caaacgggcc ctgtcttctc agcatcaagc aagaattgaa     960

attgagtcct tctatgaagg agaagacttt tctgagaccc tgactcgggc caaatttgaa    1020

gagctcaaca tggatctgtt ccggtctact atgaagcccg tccagaaagt gttggaagat    1080

tctgatttga agaagtctga tattgatgaa attgttcttg ttggtggctc gactcgaatt    1140

ccaaagattc agcaactggt taaagagttc ttcaatggca aggaaccatc ccgtggcata    1200

aacccagatg aagctgtagc gtatggtgct gctgtccagg ctggtgtgct ctctggtgat    1260

caagatacag gtgacctggt actgcttgat gtatgtcccc ttacacttgg tattgaaact    1320

gtgggaggtg tcatgaccaa actgattcca aggaacacag tggtgcctac caagaagtct    1380

cagatctttt ctacagcttc tgataatcaa ccaactgtta caatcaaggt ctatgaaggt    1440

gaaagacccc tgacaaaaga caatcatctt ctgggtacat ttgatctgac tggaattcct    1500
```

```
cctgctcctc gtggggtccc acagattgaa gtcacctttg agatagatgt gaatggtatt   1560

cttcgagtga cagctgaaga caagggtaca gggaacaaaa ataagatcac aatcaccaat   1620

gaccagaatc gcctgacacc tgaagaaatc gaaaggatgg ttaatgatgc tgagaagttt   1680

gctgaggaag acaaaaagct caaggagcgc attgatacta gaaatgagtt ggaaagctat   1740

gcctattctc taaagaatca gattggagat aaagaaaagc tgggaggtaa actttcctct   1800

gaagataagg agaccatgga aaaagctgta gaagaaaaga ttgaatggct ggaaagccac   1860

caagatgctg acattgaaga cttcaaagct aagaagaagg aactggaaga aattgttcaa   1920

ccaattatca gcaaactcta tggaagtgca ggccctcccc caactggtga agaggataca   1980

gcagaaaaag atgagttgta ggcggccgcg ggtacccacg tgtcgacctg cagccaagct   2040
```

<210> SEQ ID NO 9
<211> LENGTH: 18
<212> TYPE: PRT
<213> ORGANISM: Artificial Sequence
<220> FEATURE:
<223> OTHER INFORMATION: BiP signal sequence

<400> SEQUENCE: 9

```
Met Lys Leu Ser Leu Val Ala Ala Met Leu Leu Leu Leu Ser Ala Ala
1               5                   10                  15

Arg Ala
```

<210> SEQ ID NO 10
<211> LENGTH: 4
<212> TYPE: PRT
<213> ORGANISM: Artificial Sequence
<220> FEATURE:
<223> OTHER INFORMATION: 5' terminal sequence

<400> SEQUENCE: 10

```
Glu Glu Glu Asp
1
```

<210> SEQ ID NO 11
<211> LENGTH: 6
<212> TYPE: PRT
<213> ORGANISM: Artificial Sequence
<220> FEATURE:
<223> OTHER INFORMATION: 5' terminal sequence

<400> SEQUENCE: 11

```
Arg Ala Glu Glu Glu Asp
1               5
```

<210> SEQ ID NO 12
<211> LENGTH: 4
<212> TYPE: PRT
<213> ORGANISM: Artificial Sequence
<220> FEATURE:
<223> OTHER INFORMATION: 5' terminal sequence

<400> SEQUENCE: 12

```
Met Glu Glu Asp
1
```

<210> SEQ ID NO 13
<211> LENGTH: 4
<212> TYPE: PRT
<213> ORGANISM: Artificial Sequence
<220> FEATURE:

-continued

```
<223> OTHER INFORMATION: 3' terminal sequence

<400> SEQUENCE: 13

Lys Asp Glu Leu
1


<210> SEQ ID NO 14
<211> LENGTH: 7
<212> TYPE: PRT
<213> ORGANISM: Artificial Sequence
<220> FEATURE:
<223> OTHER INFORMATION: 3' terminal sequence

<400> SEQUENCE: 14

Leu His His His His His His
1               5
```

PROTEIN WITH ANTI-INFLAMMATORY PROPERTIES

CLAIM OF PRIORITY

This application is a divisional of U.S. patent application Ser. No. 16/007,742, filed Jun. 13, 2018, which is incorporated by reference in its entirety.

FIELD OF THE INVENTION

The present invention relates to a novel protein, its use in medicine, in particular its use in the prevention or treatment of inflammatory conditions, and processes for preparing the protein.

BACKGROUND

The anti-inflammatory properties of a human molecular chaperone known variously as binding immunoglobulin protein (BiP) or glucose-regulated protein 78 (Grp78) have been reported (Corrigall V M, Bodman-Smith M D, Brunst M, Cornell H, Panayi G S. The stress protein, BiP, stimulates human peripheral blood mononuclear cells to express an anti-inflammatory cytokine profile and to inhibit antigen presenting cell function: relevance to the treatment of inflammatory arthritis. Arthritis Rheum 2004; 50:1167-1171). The amino acid sequence of the bacterially expressed recombinant human protein differs from the known sequence of the naturally occurring protein (SEQ ID NO: 5).

BiP is a ubiquitous, endogenously expressed protein resident in the endoplasmic reticulum (ER) and required as an intracellular protein for both the correct folding of nascent polypeptides and for protection of the cell from accumulated misfolded proteins at times of ER stress. Therefore, BiP is also defined as a stress protein and a member of the heat shock protein 70 family. Upregulated during cellular stress BiP is cell surface expressed and secreted into the extracellular matrix, such that cell-free BiP may be secreted into the synovial fluid of patients with rheumatoid arthritis (Corrigall V M et al supra.,).

The gene encoding this native (naturally-occurring) BiP, p78, has been cloned and the recombinant human protein has been expressed (WO2000/21995).

WO2000/21995 discloses novel protein analogues of BiP (SEQ.1 and SEQ.2) and their utility in the treatment of inflammatory disease.

WO2006/111720 discloses the use of the same two analogues for the treatment and prevention of bone loss and resorption.

WO2002/072133 discloses the use of BiP, in particular SEQ.1 and SEQ.2 from WO2000/21995 for the treatment or prevention of an unwanted immune response, including the treatment of immune-mediated disease such as auto-immune disease, type I diabetes, thyroiditis, multiple sclerosis, lupus, Crohn's disease, hepatitis, or unwanted immune response associated with transplant organ rejection.

Although the BiP analogues (SEQ. 1 and SEQ.2) show results in a number of in vitro and in vivo animal models of inflammation, extrapolation from these models to predict what may happen in the clinic is problematic and there remains the challenge of manufacture of a protein of suitable purity and efficacy for administration to patients.

The BiP analogues SEQ. 1 and SEQ.2 (from now onwards SEQ ID NO:1 and SEQ ID NO: 2) are produced using bacterial cells but are not suitable as clinical products for human administration for several reasons. It has been reported that the 6× histidine tag on SEQ ID NO: 1, (used for protein isolation by affinity chromatography) may alter the properties, physical and functional of the protein. (Santiago F W et al, Antigenic and immunogenic properties of recombinant hemagglutinin proteins from H1N1 when produced in various protein expression systems, Vaccine, Volume 30, Issue 31, 29 Jun. 2012, Pages 4606-4616,) while the metal ions used for chelation may leach into the bloodstream if not completely removed. SEQ ID NO: 1 therefore cannot be used clinically.

Although the use of bacterial cells as a method of production is easier and cheaper than using transformed mammalian cells it has the problem of resulting in proteins that are not glycosylated and may not have the same folding as their mammalian equivalent. Furthermore, the endotoxin load in the bacterial product remains high and may cause adverse effects if administered to humans. It is principally the technical difficulty of removing the endotoxin from the product that has led to the increase in popularity of transformed mammalian cell protein production despite its cost. Purification to remove endotoxin during the manufacturing process is technically complex, expensive and time consuming. In addition, scalability of the production and purification processes can be a problem.

Accordingly, there is a need for a novel protein with anti-inflammatory and/or immunoregulatory properties based on BiP that is suitable for human administration, yet is easy to manufacture using a scalable process and also effective in therapy.

STATEMENT OF INVENTION

These needs are addressed by the novel protein of the invention.

Accordingly, an aspect of the invention provides an isolated or recombinant protein comprising the amino acid sequence according to SEQ ID NO: 3 or SEQ ID: NO: 4.

Wherever embodiments are described with the language "comprising," otherwise analogous embodiments described in terms of "consisting of" and/or "consisting essentially of" are included.

The present invention relates to an analogue of Binding Immunoglobulin Protein (BiP), SEQ ID NO: 3, shown in FIG. 4. The predicted amino acid sequence of native BiP is provided in FIG. 1 and can be found under accession number X87949 in the publicly available database NCBI Genbank. The nucleotide sequence of native BiP is shown in FIG. 2. The native amino acid sequence has a signal sequence MKLSLVAAMI LLLSAARA (SEQ ID NO: 9) attached to the n-terminus. Cleavage of the signal sequence after the alanine residue releases the mature polypeptide beginning "EEED . . . " (SEQ ID NO: 10).

The amino acid sequence of SEQ ID NO:3 differs from the sequence of native BiP in that the N-terminus begins with the sequence "RAEEED . . . " (SEQ ID NO: 11), rather than "EEED . . . " (SEQ ID NO: 10). This includes the two c-terminal amino acids of the native signal sequence (arginine and alanine). A skilled person would have no reason to include RA at the n-terminus—in the native form the active polypeptide begins at the glutamic acid residue, and it would be understood that if a skilled person was looking to provide a modified form of BiP there are multiple options, including cleaving the signal sequence at different positions and providing any number of mutations, additions or deletions.

SEQ ID NO: 4 corresponds to SEQ ID: NO: 3 with a polyhistidine affinity tag (from now onwards a His-tag) at the n-terminus of the protein (see FIG. 3). The His-tag facilitates purification of the protein by metal ion affinity chromatography.

SEQ ID NO: 3 also has significant differences from the SEQ ID NO: 1 and SEQ ID NO: 2 disclosed in WO2000/21995. As discussed above, SEQ ID NO: 1 has a His-tag at the c-terminus and the n-terminus begins "MEED . . . " (SEQ ID NO: 12). SEQ ID NO: 2 corresponds to SEQ ID NO: 1 but without the His-tag.

It has been surprisingly found that the protein of SEQ ID NO: 3 possesses potent anti-inflammatory and immunoregulatory properties that are distinct from those reported in WO2000/21995 and WO2006/111720. These significant differences would not have been expected by the skilled person. These properties are here demonstrated by relevant in-vitro and in-vivo studies. Furthermore, the protein of the invention is safe for use in humans.

Key functional differences between SEQ ID NO: 3 in accordance with the invention and SEQ ID NO: 1 of WO2000/21995 and WO2006/111720 are as follows:

1) Production of the cytokine TNFα by peripheral blood mononuclear cells is greatly reduced in the presence of SEQ ID NO: 3 as compared to SEQ ID NO: 1 (see Example 2);
2) SEQ ID NO: 1 causes downregulation of CD86 and HLA-DR, whilst SEQ ID NO: 3 showed no significant loss of HLA-DR and CD86 expression (see Example 3);
3) SEQ ID NO: 3 is suitable for use in humans and in a clinical trial no infusion reactions or serious adverse drug reactions were noted (see Example 4). By contrast SEQ ID NO: 1 is not suitable for administration to humans.
4) SEQ ID NO:3 causes a significant reduction in serum concentrations of CRP, VEGF and IL-8 in humans relative to placebo groups. This indicates that disease inflammation has been significantly reduced by the administration of SEQ ID NO: 3 (see Example 4)
5) SEQ ID NO: 3 causes an increase in CD39 expression on regulatory T cells relative to SEQ ID NO: 1; in the clinic a significant increase in the expression of CD39 on regulatory T cells from patients responding to SEQ ID NO: 3 was observed, and this was maintained for 12 weeks post-infusion (see Example 5);
6) SEQ ID NO: 3 inhibits osteoclast differentiation and resorptive activity (see Example 6);
7) There is evidence to indicate that SEQ ID NO: 3 has no overall immunosuppressive effect, unlike SEQ ID NO: 1 which reduces the recall antigen response to tuberculin PPD (see Example 7);
8) Administration of SEQ ID NO: 3 leads to longer survival of skin grafts in an animal model (see Example 8).

The invention includes isolated or recombinant proteins having one or more conservative substitutions in SEQ ID NO: 3 or SEQ ID NO: 4. A "conservative substitution" is one in which an amino acid residue is replaced with another biologically similar amino acid residue, for instance, having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). For example, substitution of a phenylalanine for a tyrosine is a conservative substitution. Methods of identifying conservative amino acid substitutions that do not adversely affect protein function are well-known in the art.

In a preferred embodiment, the isolated or recombinant BiP protein of the present invention comprises endotoxin impurities in an amount of less than 50 Endotoxin Units (EU) per mg of protein. In a preferred embodiment the isolated or recombinant protein comprises endotoxin impurities in an amount of less than 25 Endotoxin Units (EU) per mg of protein. In a preferred embodiment the isolated or recombinant protein comprises endotoxin impurities in an amount of less than 2 Endotoxin Units per mg of protein, most preferably less than 1.5 Endotoxin Units per mg of protein.

Endotoxin is detected using the Limulus Amebocyte Lysate (LAL) test to detect and quantify bacterial endotoxins extracted from the outer membrane of gram negative bacteria (Associates of Cape Cod, Liverpool, UK). The critical component of the LAL reagents used in endotoxin tests is derived from blood cells (amebocytes) of the horseshoe crab, Limulus *Polyphemus*. LAL tests are described in the Bacterial Endotoxins Test chapter in the United States Pharmacopeia (Chapter <85>) and in the equivalent chapters in the European Pharmacopoeia (Chapter 2.6.14) and the Japanese Pharmacopoeia (General Tests, No. 4.01).

The protein of the invention is non-glycosylated or substantially non-glycosylated, in contrast to the native protein which is glycosylated.

In a further aspect, the present invention provides an isolated or recombinant nucleic acid molecule encoding a recombinant protein consisting of the amino acid sequence according to SEQ ID: NO. 4.

Preferably the isolated or recombinant nucleic acid molecule according to claim 3 consists of the nucleic acid sequence according to SEQ ID: NO 8.

An additional aspect provides a recombinant vector comprising the nucleic acid molecule as defined above.

The vector may comprise a promotor and/or an operator sequence. The vector may comprise non-mammalian sequences, for example sequences from bacteria or yeast. The vector may comprise a non-mammalian promotor and/or operator sequence, such as a bacterial or yeast promotor and/or operator sequence.

In a further aspect, the invention provides an isolated or recombinant protein as defined above for use in medicine or veterinary medicine. The protein of the invention may be for use in human or non-human animals.

In a yet further aspect, the invention provides an isolated or recombinant protein as defined above for use in the treatment and/or prevention of an inflammatory condition. Preferably the treatment and/or prevention of an inflammatory condition is achieved without significant immunosuppression. In one embodiment the treatment and/or prevention of an inflammatory condition is achieved without significant immunosuppression as measured by T-lymphocyte activity relative to activity prior to administration of the protein. In one embodiment there is no significant inhibition of T-cell proliferation to a recall antigen such as tuberculin purified protein derivative or a mitogen such as phytohaemagglutinin (PHA) or anti-CD3 or anti-CD28 antibody coated beads.

In a preferred embodiment, the inflammatory condition is selected from rheumatoid arthritis, psoriatic arthritis, juvenile idiopathic arthritis, ankylosing spondylitis, rejection of a transplant of an organ, skin, tissue, blood, serum, plasma or cells, or inflammatory bowel disease such as Crohn's disease.

In a particularly preferred embodiment the inflammatory condition is selected from rheumatoid arthritis, psoriatic arthritis, or juvenile idiopathic arthritis.

In one embodiment the isolated or recombinant protein is for use in treating or preventing diseases of dysregulation of bone metabolism, for example osteoporosis, bone loss, bone resorption, Paget's disease, breast cancer, bone cancer or bone loss associated with cancer. Metastatic breast cancer is known to be associated with bone loss (See nationalbreastcancer.org/metastatic-breast-cancer).

In another aspect, the isolated or recombinant protein as defined above is for use in the prevention of prosthetic joint loosening.

In one embodiment of the isolated or recombinant protein as defined above for the use defined above, the use comprises administering the protein as a dose of from 1 mg to 1 g, optionally 1 mg to 500 mg, optionally 1 mg to 50 mg, optionally 1 to 15 mg.

The dose may be 1 mg, 5 mg or 15 mg.

The protein may be administered as a single dose or as multiple doses.

The dose may be administered as a single intravenous infusion for a period of time of 0.5 to 3 hrs, optionally 1 to 2 hrs, preferably 1 hr.

In a preferred embodiment a dose of 1 mg, or 5 mg or 15 mg is administered to a patient for a period of time of 1 hr.

In an alternative embodiment, multiple doses may be administered to the patient, wherein the interval between administration of each dose is at least 1 hr, or at least 2 hrs, or at least one day, or at least 1 week.

Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

In a further aspect the invention provides a pharmaceutical composition comprising the isolated or recombinant protein as defined in any preceding claim and one or more pharmaceutically-acceptable excipients, adjuvants or carriers. The one or more pharmaceutically-acceptable excipients, adjuvants or carriers are not especially limited, and suitable excipients, adjuvants or carriers would be known to a person skilled in the art.

Any suitable route of administration can be used. For example, any of oral, topical, parenteral, ocular, rectal, vaginal, inhalation, buccal, sublingual and intranasal delivery routes may be suitable.

Pharmaceutical compositions for parenteral administration may be preferred. The proteins and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. Intravenous administration is particularly preferred.

Pharmaceutical compositions can comprise a pharmaceutically acceptable carrier, such as physiological saline. Suitable pharmaceutical compositions can comprise one or more of a buffer (e.g. acetate, phosphate, citrate), a surfactant (e.g. polysorbate), a stabilizing agent (e.g. human albumin, polyol, amino acid), a preservative (e.g. sodium benzoate), and/or other conventional solubilizing or dispersing agents Pharmaceutical compositions of the invention may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In a preferred embodiment the pharmaceutical composition comprises phosphate buffered saline at pH 7.2 to 7.6, most preferably pH 7.4. In one embodiment the pharmaceutical composition comprises 0.9% w/v saline.

In one embodiment the pharmaceutical composition comprises the isolated or recombinant protein in an amount of from 2.0 to 50.0 mg/mL, optionally 2.0 to 10.0 mg/mL, preferably in an amount of about 5.0 mg/mL.

Typically, the pharmaceutical composition is suitable for intravenous administration. In a further aspect, the invention provides a method of treating and/or preventing a condition as defined above in a patient comprising the step of administering to a patient in need thereof an effective amount of an isolated or recombinant protein as defined above or a pharmaceutical composition as defined above.

Terms such as "treat" or "treatment" or "treating" refer to therapeutic measures that cure, slow down, lessen symptoms of, and/or halt progression of an undesired physiological condition, a diagnosed pathologic condition, a disease, or a disorder. Thus, those in need of treatment include those already with the condition, disease, or disorder. In certain embodiments, a subject is successfully "treated" for a condition, disease, or disorder if the patient shows, e.g., total, partial, or transient alleviation or elimination of symptoms associated with the condition, disease or disorder; diminishment of the extent of the condition, disease, or disorder; stabilization (i.e., not worsening) of the condition, disease, or disorder; delay in onset or slowing of progression of the condition, disease, or disorder; amelioration of the condition, disease, or disorder, including partial or total remission; and/or prolonging survival, as compared to expected survival if not receiving treatment.

"Prevent" or "prevention" or "preventing" refer to prophylactic or preventative measures that avert and/or slow the development of a targeted pathologic condition, disease, or disorder. Thus, those in need of prevention include those prone to having or susceptible to the condition, disease, or disorder. In certain embodiments, a condition, disease, or disorder is successfully prevented if the patient develops, transiently or permanently, e.g., fewer or less severe symptoms associated with the condition, disease, or disorder, or a later onset of symptoms associated with the condition, disease, or disorder, than a patient who has not been subject to the methods of the invention.

In one embodiment the patient is further administered one or more therapeutic agents or when the protein is provided in combination with one or more therapeutic agents. In a preferred embodiment the therapeutic agent is selected from disease modifying agents, analgesics, anti-inflammatory agents, immunotherapeutic agents, antibiotics, antibodies and steroids. In a particular embodiment the therapeutic agent is a disease-modifying anti-rheumatic drug (DMARD).

In a further aspect the invention provides a method for preparing a recombinant protein consisting of the amino acid sequence according to SEQ ID NO: 3, the method comprising:

a) transforming a microorganism with the recombinant vector as defined in claim 6;
b) culturing the microorganism leading to the production of a protein according to SEQ ID NO: 4;
c) lysing the microorganisms to release the protein;
d) treating the lysate with a detergent to remove endotoxin;
e) isolating and purifying the protein using immobilized metal affinity chromatography, wherein the immobilized metal is cobalt; and
f) contacting the purified protein with a diaminopeptidase enzyme, wherein the diaminopeptidase cleaves the histidine tag from the N-terminus of the protein; and
g) separating the cleaved protein from the histidine tag.

Preferably the microorganism is a bacterium, most preferably *Escherichia coli.*

In one preferred embodiment the microorganism is cultured in a medium free from, or substantially free from animal-derived products.

Typically, the method comprises one or more further steps of treating the protein with a detergent to remove endotoxin. The detergent may be 1,1,3,3-(tetramethylbutyl)phenyl-polyethylene glycol. As an alternative the protein may be treated with arginine in order to remove endotoxin.

The above-mentioned method is preferably for producing a protein having less than 25 Endotoxin Units per mg of protein, optionally less than 2 Endotoxin Units per mg of protein. The addition of detergent or arginine enables removal of endotoxin.

Step f) occurs at a temperature suitable for the activity of the diaminopeptidase enzyme, preferably approximately 37° C.

Typically step g) is carried out using immobilized metal affinity chromatography, wherein the immobilized metal is cobalt. The cleaved His-tag binds to the column, and the purified protein elutes from the column.

Preferably the method does not include more than one freeze-thaw steps. Preferably, the protein is not frozen at any stage of the method. If it is necessary to store the protein between the steps of the method, the protein is stored at a temperature of from 2 to 8° C.

In one embodiment the method further comprises one or more filtration, purification or concentration steps.

In one embodiment the cells are lysed by shearing, in particular using a French press.

In another embodiment the protein of the invention is produced using host cells other than bacterial. In one embodiment, the protein of the invention is produced using cells derived from yeast, insect or fungi. In a preferred embodiment the protein of the invention is produced using mammalian cells.

Non-limiting examples will now be described with reference to the following figures:

FIG. 1 shows the amino acid sequence of native BiP (SEQ ID NO: 5). The primary structure of BiP is composed of 664 amino acids. At the N' terminus the leader sequence of 18 amino acids (underlined) is cleaved during post-translational changes.

FIG. 2 shows the nucleotide sequence of native BiP (SEQ ID NO: 6). The BiP gene is 2.5 kilobases.

FIG. 3 shows SEQ ID: NO 4, the protein of the invention including the His-tag (bolded and underlined) at the N-terminus prior to cleavage during purification.

FIG. 4 shows SEQ ID: NO 3, the protein of the invention (not including the His-tag)

Figure 5A:
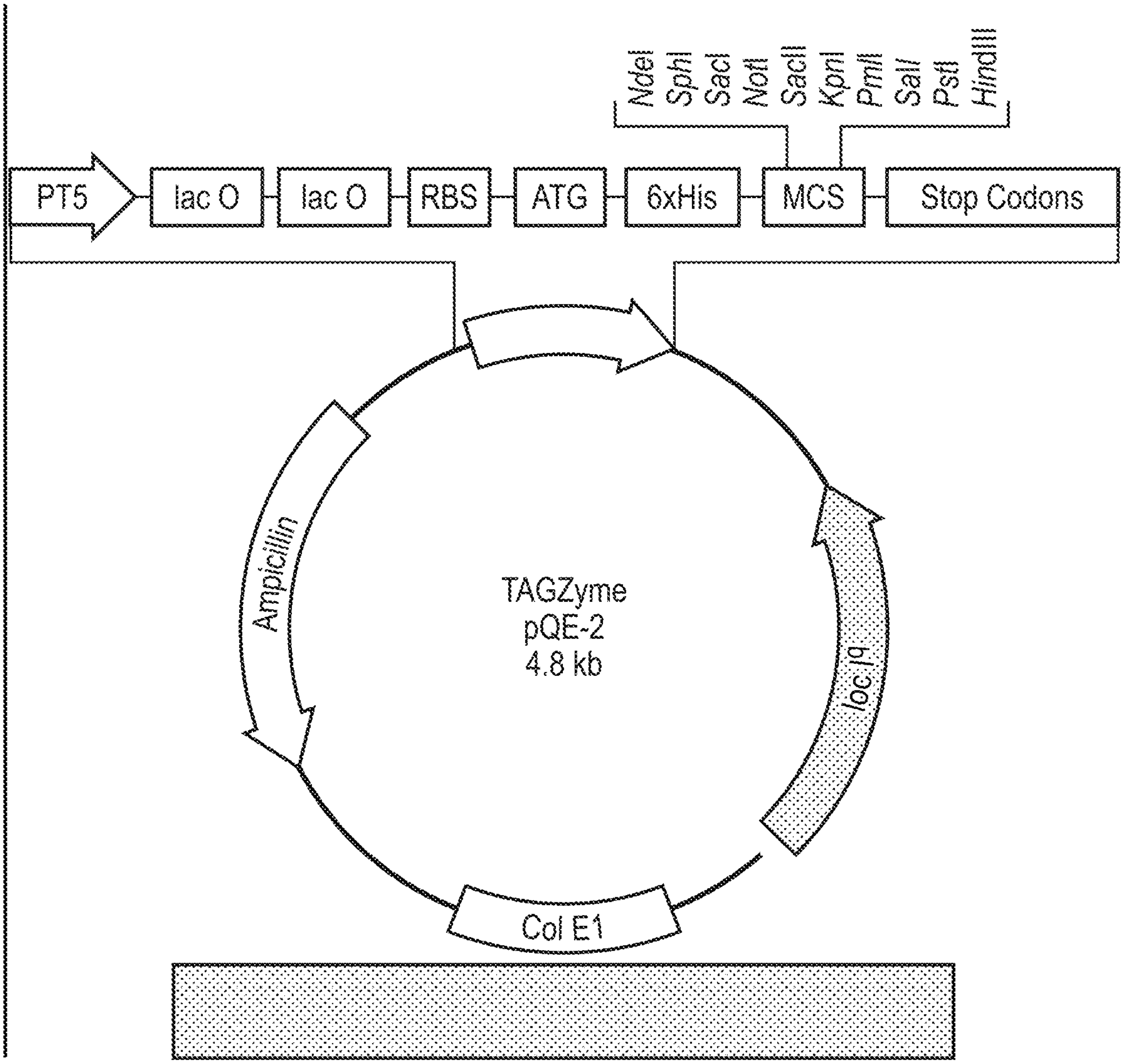

FIG. 5A shows the recombinant vector pQE-2 used for cloning the native BiP gene. A schematic of the vector used shows the site for the histidine tag and the cleavage sites for the restriction enzymes. FIG. 5B shows the BiP Sequence (SEQ ID NO: 8) cloned into NdeI/NotI site of vector pQE-2.

FIG. 6 shows an alignment of the amino acid sequence of the protein of SEQ ID NO: 4 (top) in accordance with the invention with the amino acid sequence of the native protein (SEQ ID NO: 5; bottom).

FIG. 7 shows SEQ ID NO: 1, SEQ 1 from WO00/21995.

FIG. 8 shows SEQ ID NO: 2, SEQ 2 from WO00/21995.

FIG. 9 shows SEQ ID NO: 7.

Figure 10:
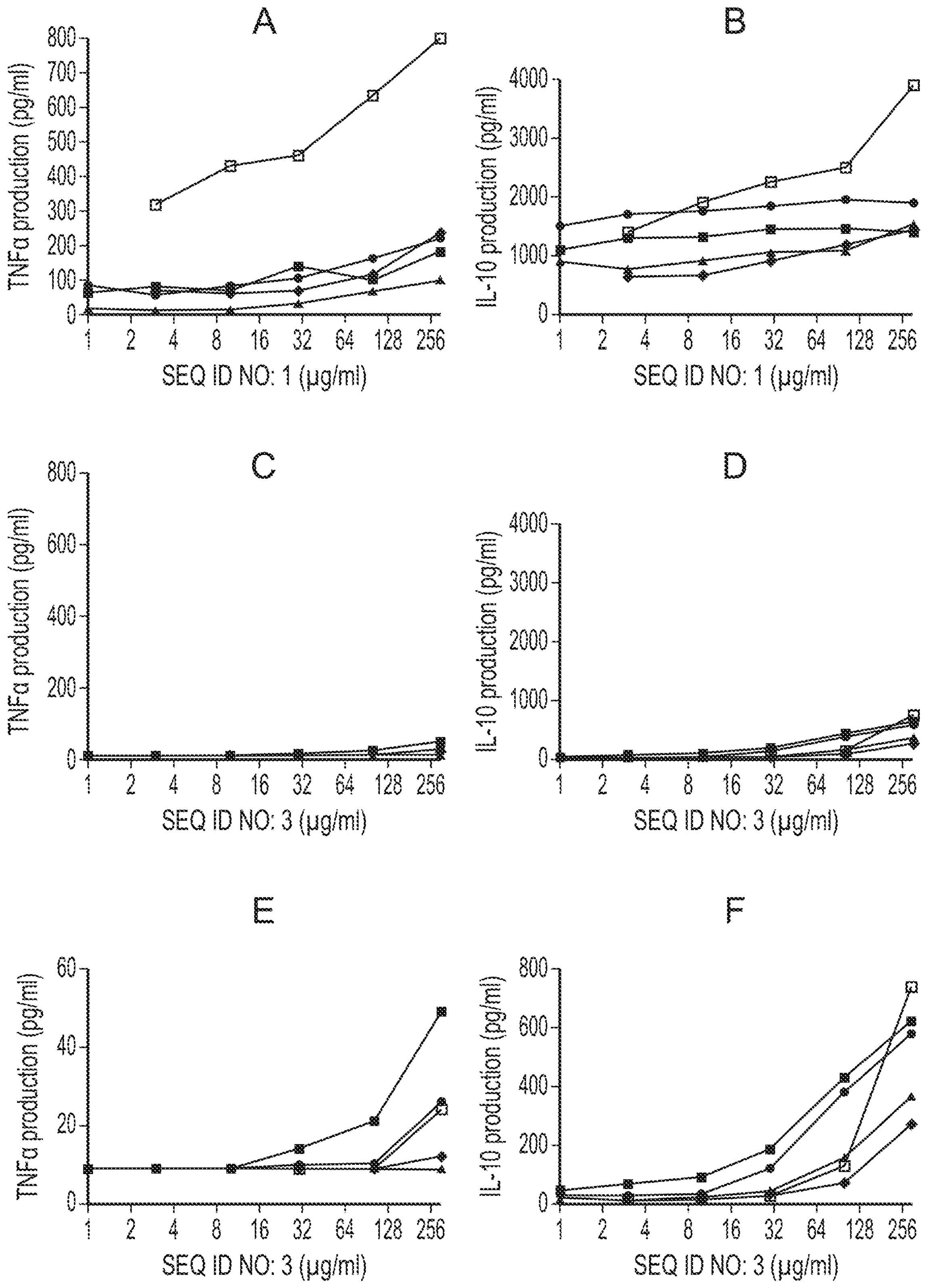

FIGS. 10A-10F show a comparison of cytokines production induced by SEQ ID NO: 1 and SEQ ID NO: 3. Peripheral blood mononuclear cells were cultured for 24 h in the presence of either SEQ ID NO: 1 (FIGS. 10A, 10B) or SEQ ID NO: 3 (FIGS. 10C, 10D, 10E and 10F) at the concentrations shown. PBMC from 4 healthy controls (solid symbols) and one rheumatoid arthritis patient (open symbol) were used. At 24 h the supernatants were collected and the production of tumour necrosis factor (TNF) a and Interleukin (IL) 10 were quantified by enzyme linked immunosorbent assay (ELISA). FIGS. 10E and 10F show the same data as FIGS. 10C and 10D but with an individual y axis scale to allow the identification of the five samples to be observed.

Figure 11:
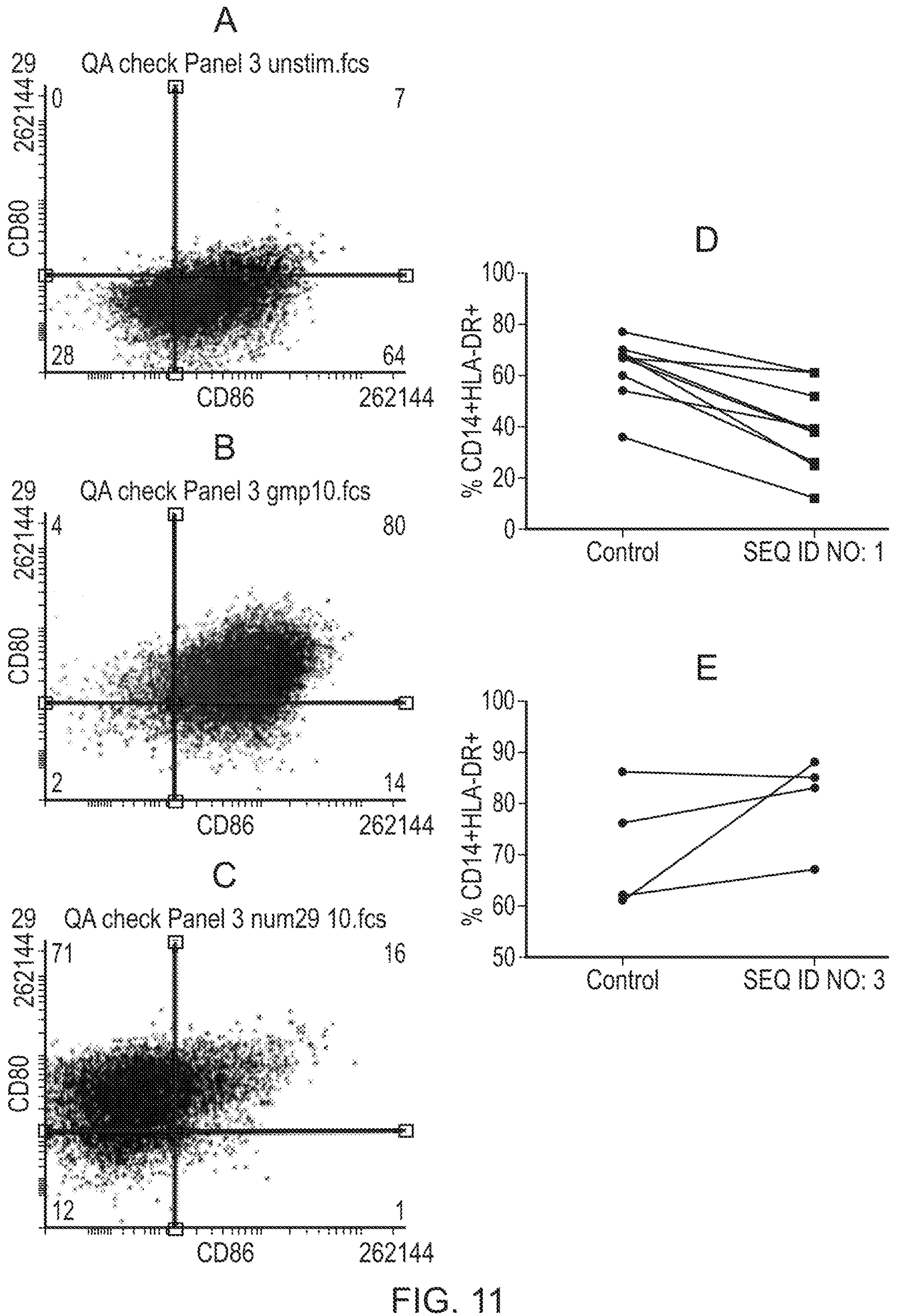

FIGS. 11A-11E show data from experiments using peripheral blood mononuclear cells (PBMC) cultured alone or with SEQ ID NO:3 or SEQ ID NO: 1 for 24 hours before flow cytometric analysis using fluorochrome conjugated antibodies, anti-CD80.phycoerythrin, anti-CD86. fluorescein isothiocyanate (FITC) or HLA-DR.FITC. In all cases the PBMC samples were live gated to access the CD14 population only. PBMC were cultured either untreated (FIG. 11A); in the presence of SEQ ID NO:3 (FIGS. 11B and 11E); or in the presence of SEQ ID NO: 1 (FIGS. 11C and 11D). SEQ ID NO: 1 showed down-regulation of CD86 and also HLA-DR. In contrast, SEQ ID NO: 3 in accordance with the invention showed no significant loss of HLA-DR and CD86 expression.

Figure 12:
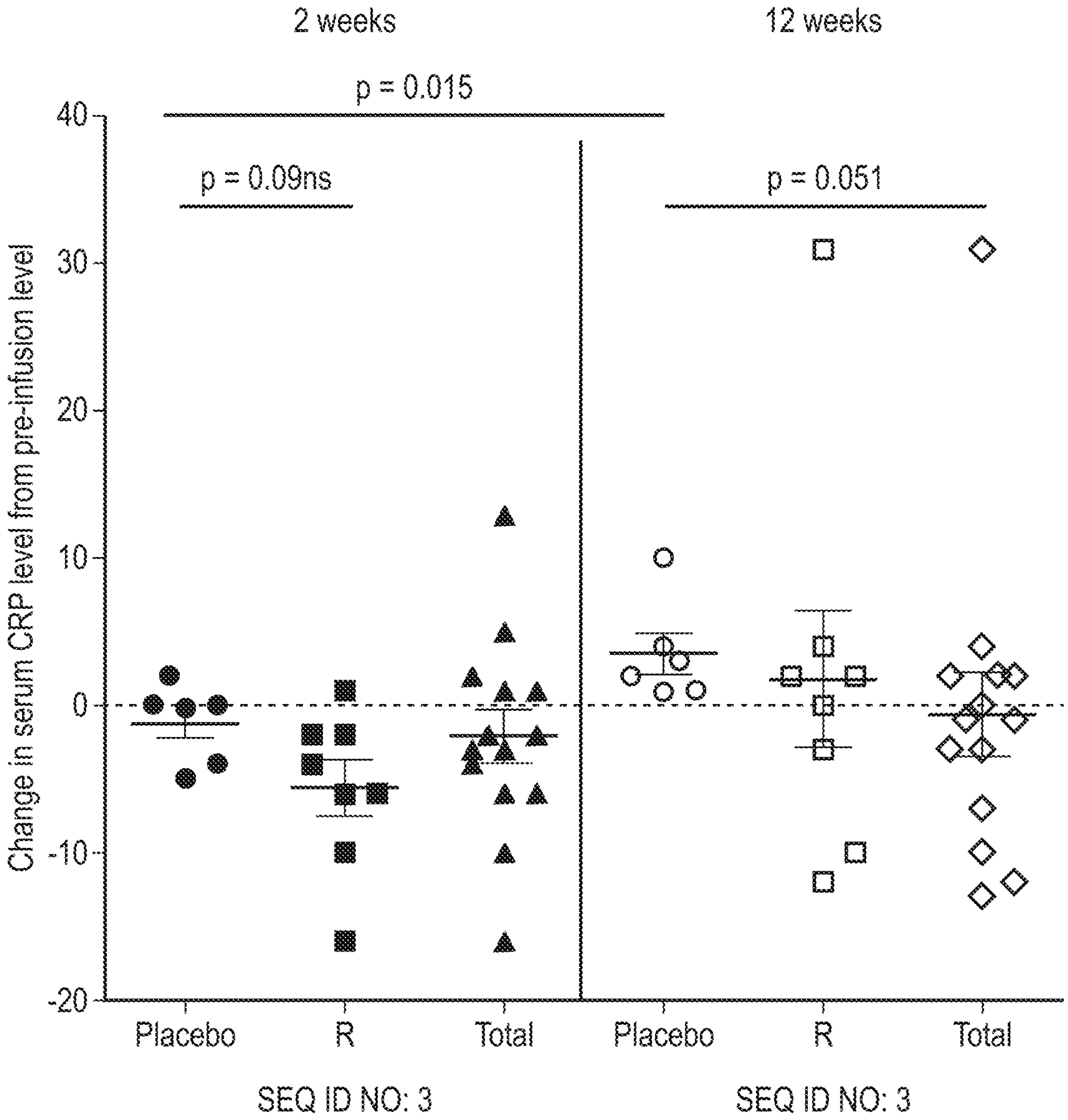
Figure 14:
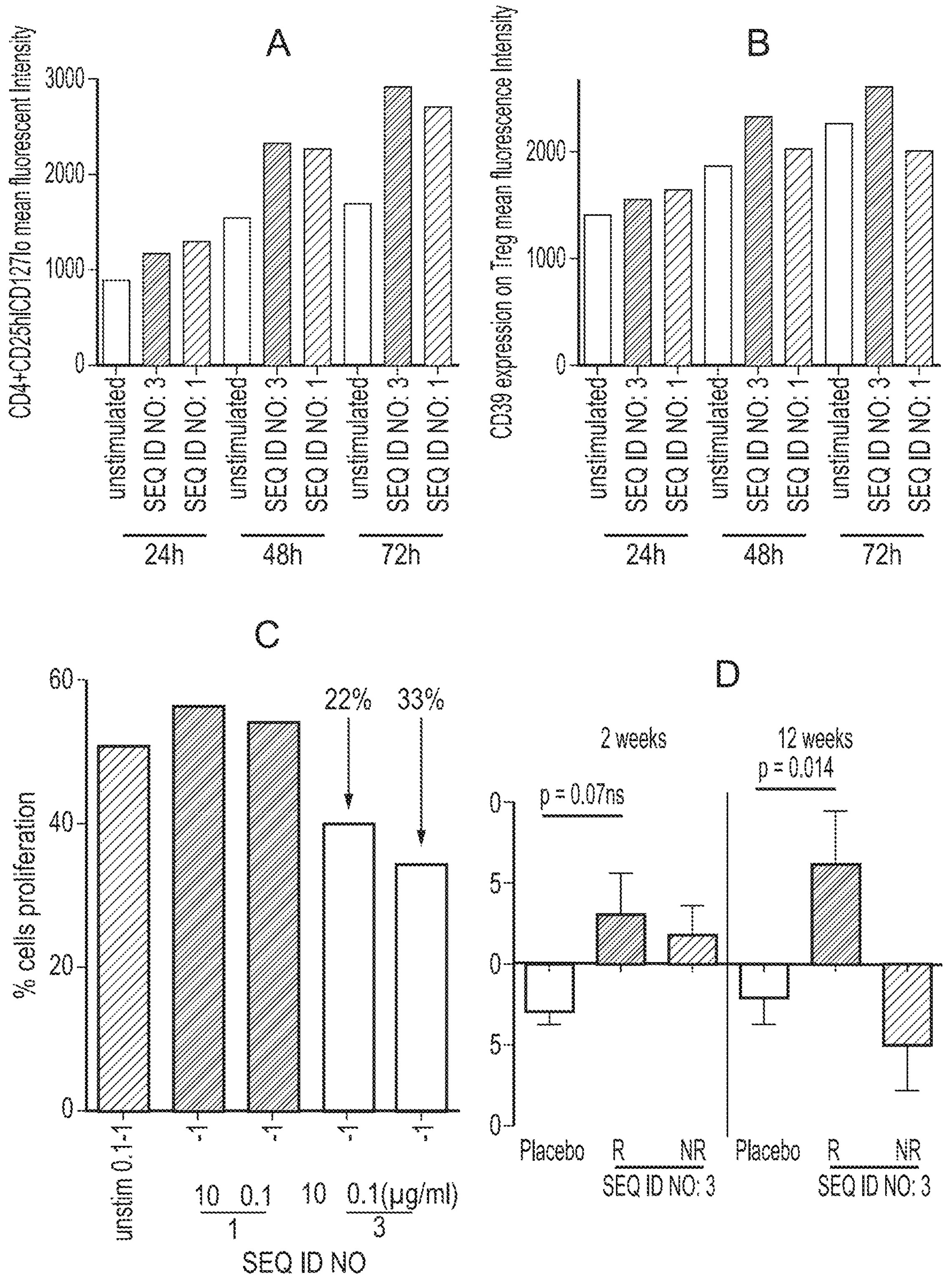

FIG. 12 shows the effect of SEQ ID NO: 3 on serum C-reactive protein (CRP) levels taken from patients in the first human clinical trial for SEQ ID NO: 3. Three groups of patients are shown, placebo, active responders (R) and all patients who received SEQ ID NO: 3. The change in CRP serum levels from pre-infusion level at 2 weeks and 12 weeks post infusion were measured for the placebo group, the responding group and all patients treated with SEQ ID NO: 3. At 12 weeks a significant drop in the level of CRP was noted in patients treated with SEQ ID NO: 3. * this patient dropped her concomitant methotrexate medication, a protocol violation.

FIGS. 13A-13B show changes in biomarker levels in SEQ ID NO: 3 treated patients. Serum concentrations of VEGF and IL-8 were measured by Luminex bead technology and the change from pre-infusion serum concentration calculated for each patient at 2 and 12 weeks. (FIG. 13A) Change in VEGF concentration; (FIG. 13B) change in IL-8 concentration. Data show placebo group (n=6), responder group (R) [n=8 (2 weeks) and 6 (12 weeks)] and the total patient group treated with SEQ ID NO: 3 [n=14 (2 weeks) and 12 (12 weeks)] who remained in the study at 12 weeks. Range of concentration (all patients) VEGF, 4-195 μg/ml; and for IL-8, 0.7-19 μg/ml.

FIGS. 14A-14D show upregulated expression of CD39 a marker of increased regulatory T cell functional efficiency. Peripheral blood mononuclear cells from a RA patient were set up in culture either unstimulated (open bars) or with SEQ ID NO: 1 (10 μg/ml) (crosshatched bars) or SEQ ID NO: 3 (10 μg/ml) (black bars). After 24 h, 48 h or 72 h cells were removed from culture and stained with a panel of fluorochrome conjugated antibodies for CD45, CD3, CD4, CD25, CD127 and CD39. Cells were analysed on a FACSCanto flow cytometer (BD Biosciences). The results are expressed as a the mean fluorescent intensity (MFI) for: (FIG. 14A) CD25 hi and CD127lo cells after using multiple live gates to access live, CD45+, CD3+, CD4+ cells; (FIG. 14B) the expression of CD39 by the CD45+CD3+CD4+ CD25hiCD127lo population in FIG. 14A. (FIG. 14C) PBMC (106/ml) were pre-treated for 96 h in culture with SEQ ID NO: 1 (10 or 0.1 μg/ml) or SEQ ID NO: 3 in accordance with the invention (10 or 0.1 μg/ml), washed and added to fresh autologous CFSE stained T cells and stimulated with anti-CD3 and anti-CD28 antibody coated beads. The ratio of pre-treated T cells to responder T cells was 1:10. The cells were analysed for reduction in CFSE MFI using Cellquest software on a FACSCalibur flow cytometer (BD Biosciences) after 3 days. No inhibition of response was observed where T cells had been pre-incubated with SEQ ID NO: 1 but up to 30% reduction in response was observed with cells pre-incubated with SEQ ID NO: 3. (FIG. 14D) In the RAGULA clinical trial, whole blood samples from placebo and SEQ ID NO: 3 treated rheumatoid arthritis patients, responder (R) or non-responder (NR) were monitored for the change in expression of CD39 on Treg cells (live, CD45+CD3+CD4+CD25 hi CD127lo) over 12 weeks. Results are expressed as a % change in cell surface expression at the indicated time-points, from pre-infusion. After a single infusion, CD39+ expression was significantly raised for at least 12 weeks post-infusion.

FIGS. 15A-15F show the results of flow cytometry analysis of expression of CD115/c-Fms (FIG. 15A) and RANK (FIG. 15B) protein levels by M-CSF-dependent human osteoclast precursors cultured in the absence or presence of SEQ ID NO: 1 (2 μg/ml) for 48 h. Representative samples showing mean fluorescence intensity: Dotted line, untreated control; Heavy solid line, RANKL activated control; light solid line, RANKL activated SEQ ID NO: 3 treated cells (n=4). (FIG. 15C) qPCR analysis of c-fms and RANK expression following 48 h treatment of murine M-CSF-dependent osteoclast precursors with SEQ ID NO: 1 (2 μg/ml). Data show the mean±SEM of duplicate experiments using specific primers and normalized to β-actin. *$p<0.05$. (FIG. 15D) Western blot analysis showing expression of pERK and pp38 in human osteoclast precursors in response to RANKL (10 ng/ml) for the indicated times in cells cultured in the absence or presence of SEQ ID NO: 1 (2 μg/ml, 48 h). (FIG. 15E) Expression of RANKL-induced PERK in cultures containing mature human osteoclasts cultured in the absence or presence of SEQ ID NO: 1 (2 μg/ml, 48 h). (FIG. 15F) Western blot analysis showing expression of transcription factors c-Fos and NFATc1 in response to RANKL (10 ng/ml) in osteoclast precursors and mature osteoclasts treated in the absence or presence of BiP (2 μg/ml). Total ERK and p38 proteins, and GAPDH were used as loading controls as indicated. *$p<0.01$. This demonstrates that SEQ ID NO: 1 downregulates CD115 and RANK cell surface expression and downstream signalling in human osteoclast precursors.

Figure 16:
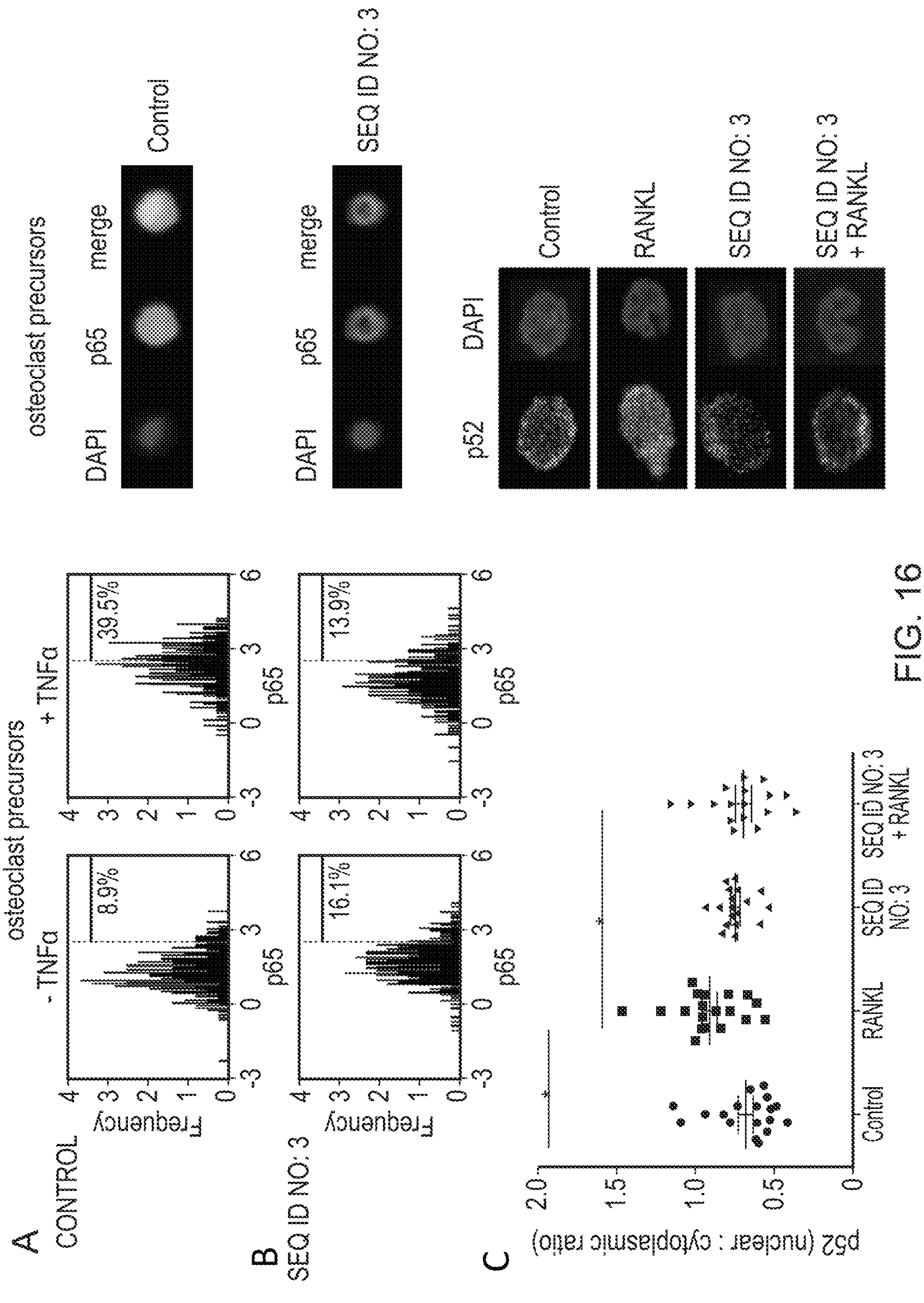

FIGS. 16A-16C show that SEQ ID NO: 3 inhibits nuclear translocation of NF-κB p65 and p52 in osteoclast precursors and THP1 monocytes following TNFα and RANKL stimulation. M-CSF-dependent (FIG. 16A) human osteoclast precursors or (FIG. 16B) THP-1 cells were pre-treated for 1 h in the absence (Co) or presence of SEQ ID NO: 3 (10 μg/ml) (FIG. 16A, 16B) and then stimulated with TNFα (10 ng/ml) for 10 min. (FIG. 16C) pre-osteoclast were cultured in the presence or absence of SEQ ID NO: 3 (10 μg/ml) with or without RANKL (50 ng/ml) for 4 h. Cells were fixed and processed for flow cytometry, imaging flow cytometry or confocal microscopy following staining for NF-κB p65 (A, B) or p52 (FIG. 16C) with DAPI counterstain. Panels on the right of each figure section show confocal images of nuclear translocation of p65 and p52 in a representative single cell, showing the absence of nuclear translocation in SEQ ID NO: 3-treated cells. *$p<0.01$, n=3.

Figure 17:
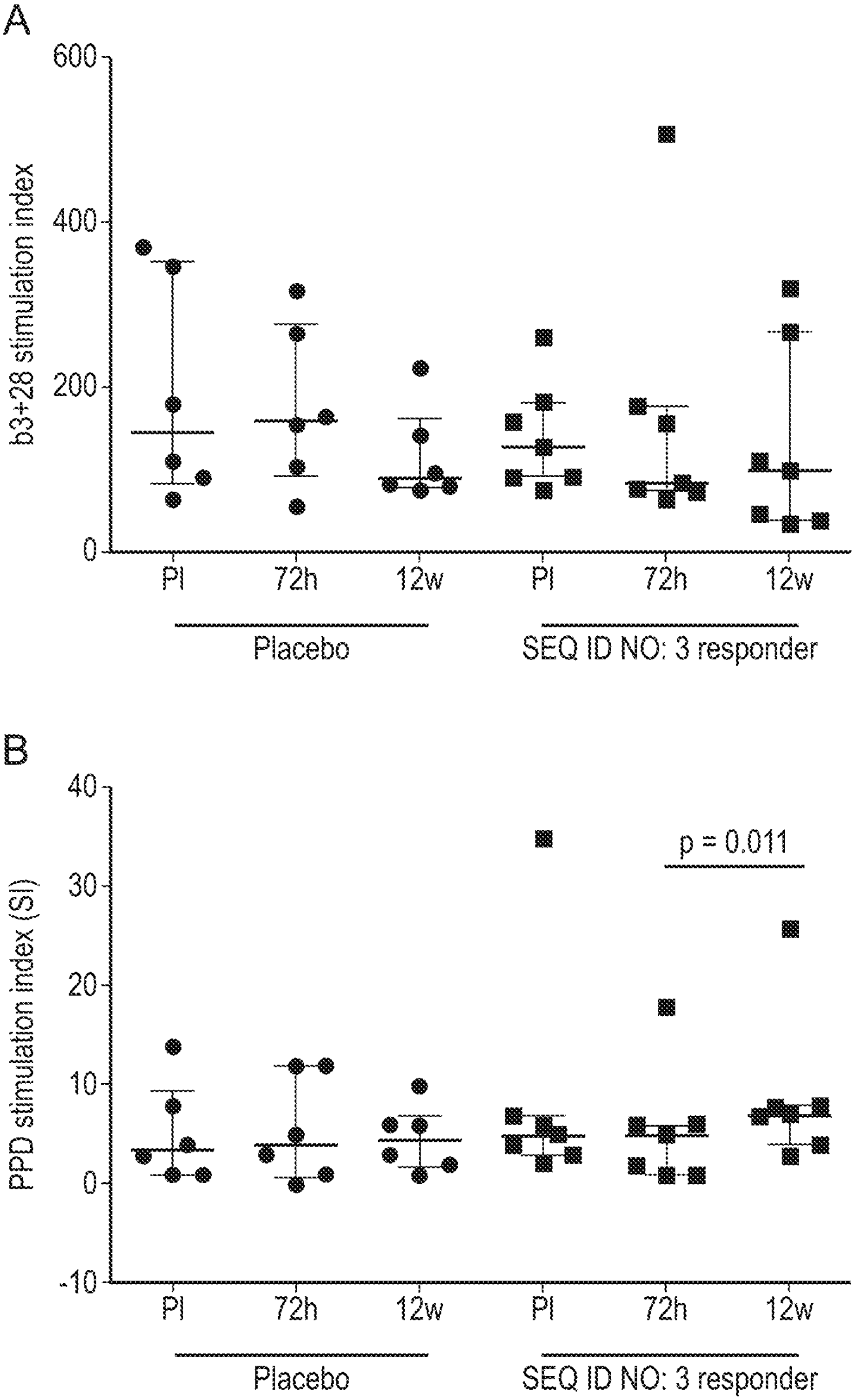

FIGS. 17A-17B: Following treatment with SEQ ID NO: 3 or placebo the immune response of patients was measured using PBMC culture stimulated to detect T cell responses to a maximal stimulus, anti-CD3 and anti-CD28 antibody coated beads (3 day culture) (FIG. 17A) or recall antigen, tuberculin PPD (5 day culture) (FIG. 17B). Activation was measured by uptake of tritiated thymidine for the last 24 h of culture.

Figure 18:
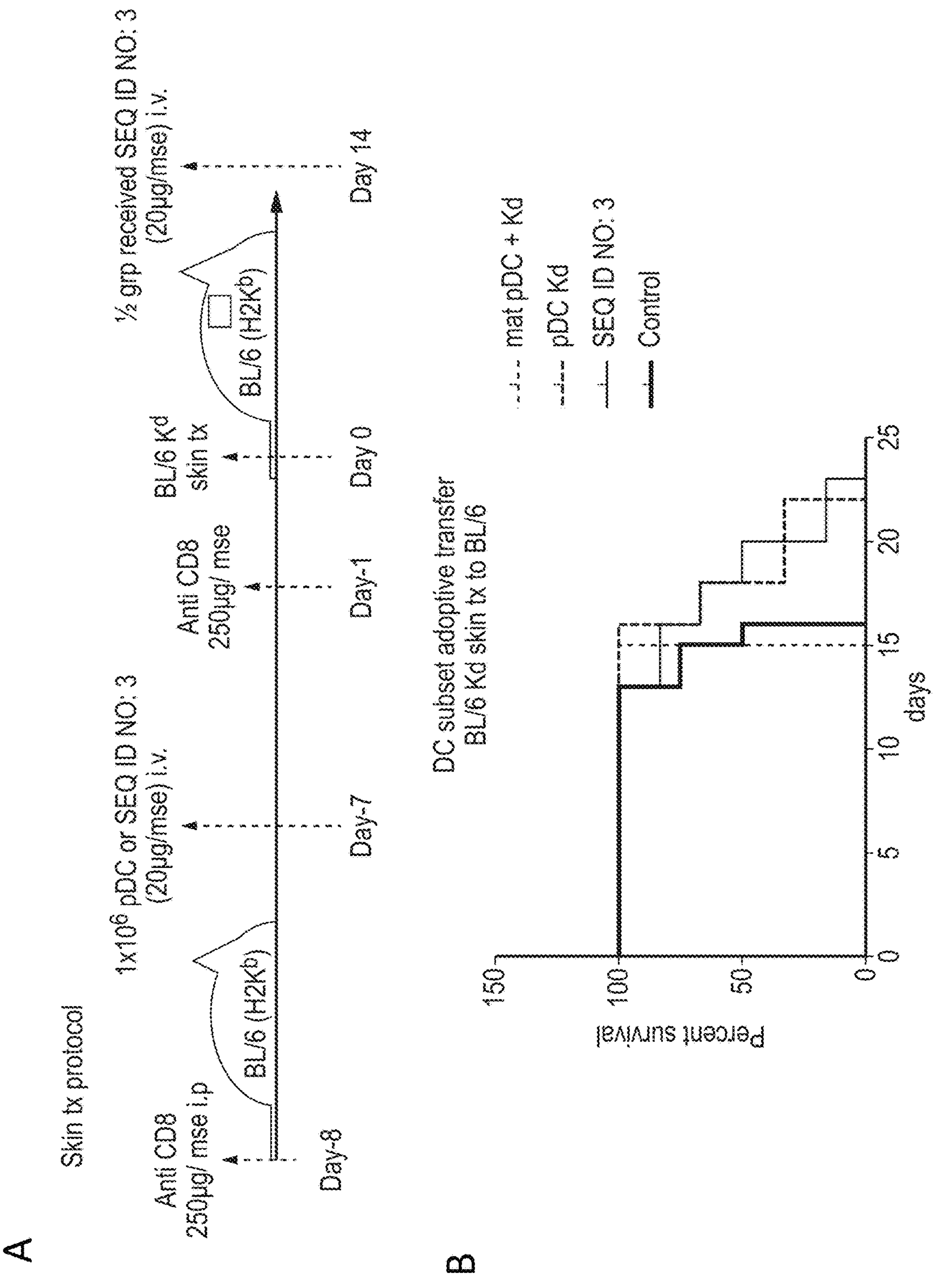

FIG. 18A shows a schematic representation of the protocol and results of a murine skin transplantation experiment. FIG. 18B shows survival analysis in a Kaplan Meier graph This demonstrates that SEQ ID NO: 3 extended the survival of 5/6 of the grafts beyond that of the control group with 50% grafts surviving for approximately 30% longer than the control mice grafts.

Figure 19:
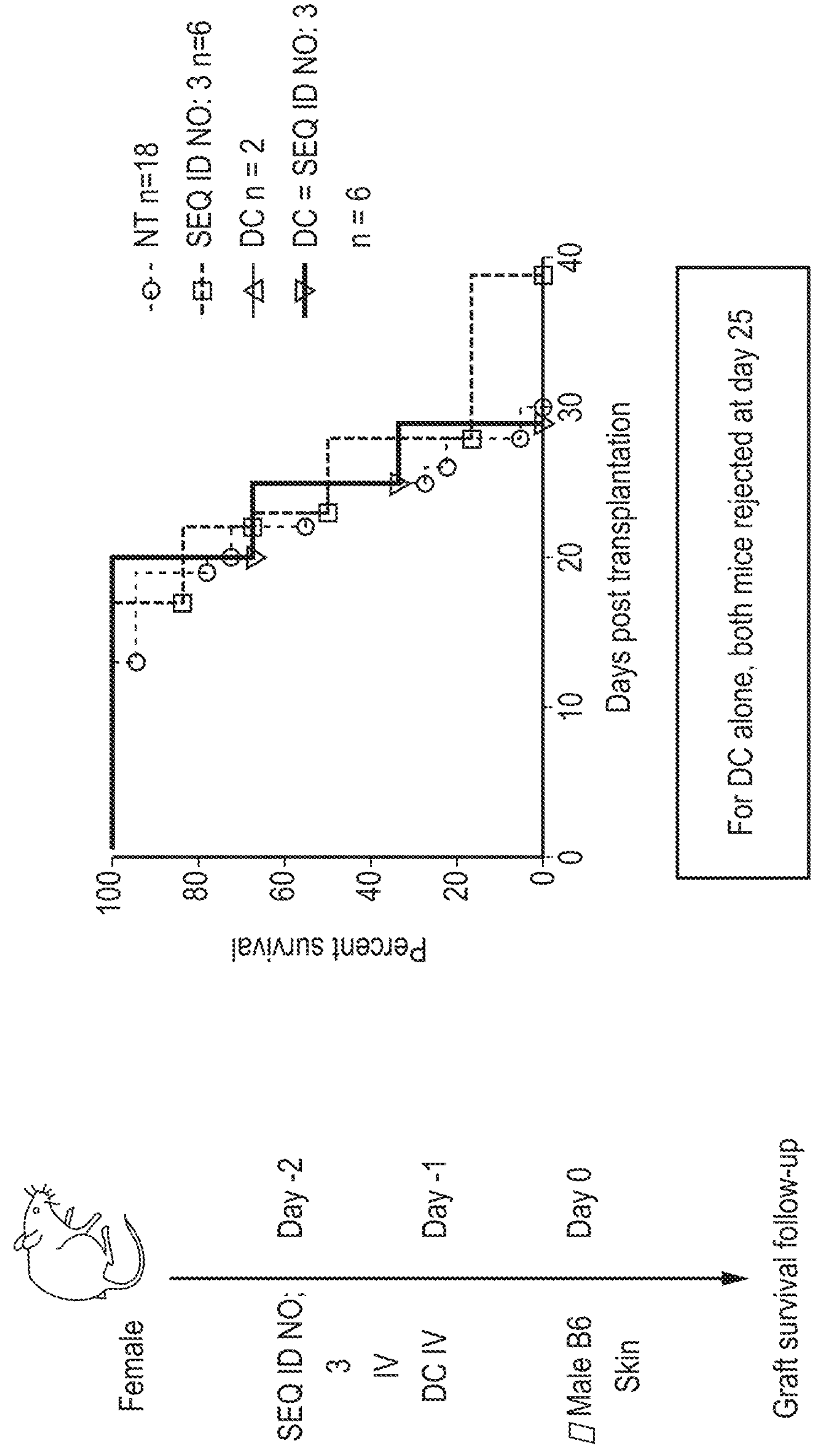

FIG. 19 shows a schematic of a second transplantation exploratory experiment. Again, SEQ ID NO: 3 administration leads to longer survival of skin grafts in comparison with those animals given modified dendritic cells (DC). Mixing DC administration with SEQ ID NO; 3 was not beneficial.

Figure 20:
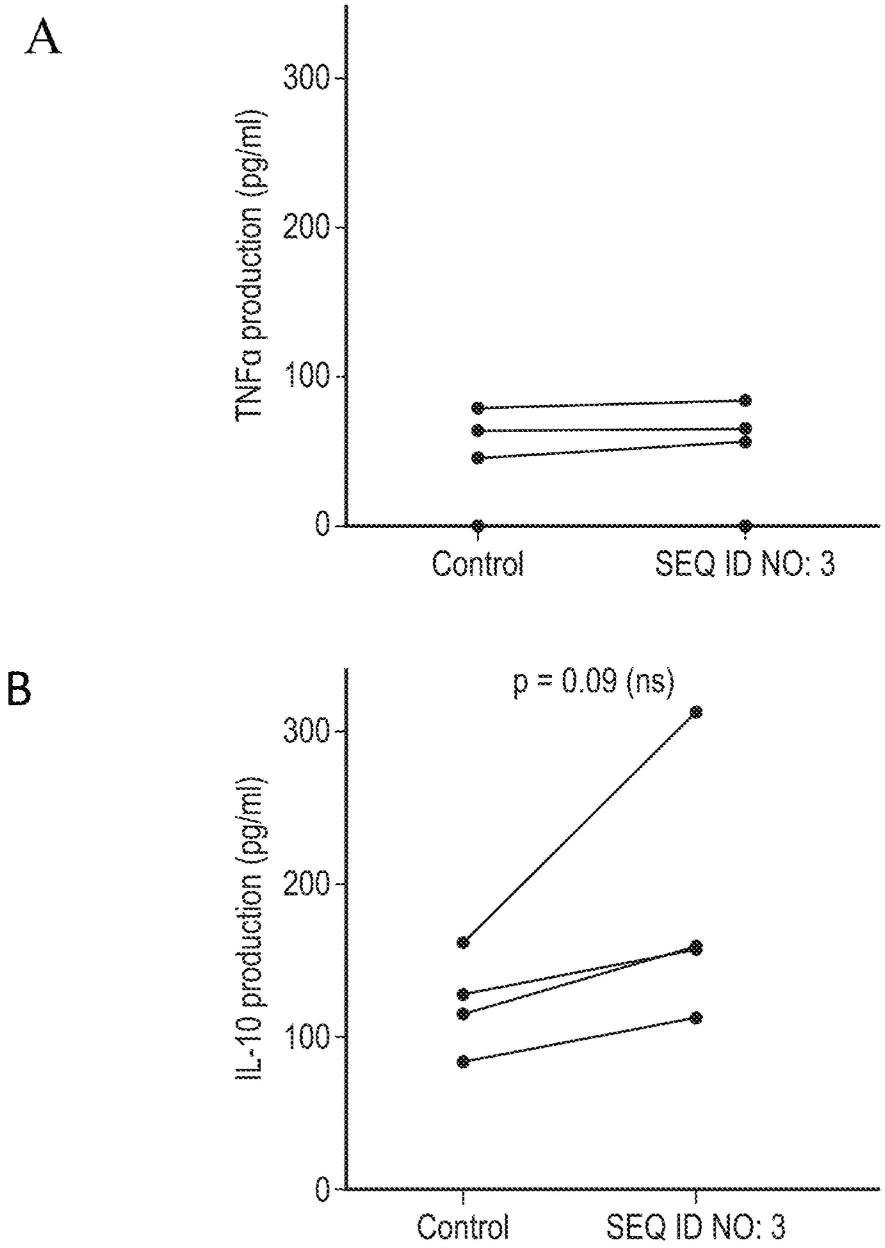

FIGS. 20A-20B show cytokine production by periprosthetic tissue cultured with and without SEQ ID NO: 3. Small pieces of similar size were cut from periprosthetic tissue taken during revision surgery after prosthetic joint loosening and with the patients full informed consent. The tissue was culture for 24-72 h either in the absence (control) or presence of SEQ ID NO: 3 (20 μg/ml). Cytokines tumour necrosis factor (TNF) a or interleukin (IL) 10 were quantified by commercial enzyme linked immunosorbent assay (ELISA) (PharMingen, BD, Oxford, UK). The two graphs show that whereas the amount of TNFα in the control cultures and the SEQ ID NO: 3 cultures show little change in all the 4 cultures, there is an increase in IL-10 production.

EXAMPLES

Example 1: Preparation of Protein of the Invention

The BiP gene was modified to place a His-tag at the N terminal end of the molecule. The 6× Histidine-tag was situated so that it could be removed by enzymatic digestion by a diaminopeptidase following affinity purification of the protein on a cobalt column. Nickel was not used because nickel could lead to an allergic reaction if sufficient remained to contaminate the preparation. A combination of temperature changes and detergent was used to efficiently remove endotoxin.

Yield and Purification

The yield is greatly improved as is the purity of the protein by the removable His-tag system.

TABLE 1

Yield of SEQ ID NO: 3 from bacterial pellet:

| Time Point | Pellet weight taken (g) | BIP (SEQ ID NO: 3) Yield (mg/g) |
|---|---|---|
| Day 0 | 2.4 g | 19.6 |
| 2 months | 60 g | 31.9 |
| 8 months | 2.4 g | 24.2 |

TABLE 2

Purity and yield of SEQ ID NO: 3

| Test | Result |
|---|---|
| Protein concentration | 5.45 mg/ml |
| Endotoxin | 1.51 EU per mg of protein |
| Filter Integrity Test of Filter used for sterile filtration of drug substance | 3900 mBar |
| Bioburden | No Growth |

Comparative Example; Preparation of SEQ ID: NO 7

During the development of the protein of the invention, it was decided that the molecule must have the correct KDEL sequence at the C' terminal and must have no other tag attached to the protein. This protein was prepared in accordance with standard recombinant techniques known to a person skilled in the art. However, there was too little protein, the purity was too low and almost all of the biological activity had been lost. Accordingly, the protein could not be used.

SEQ ID NO: 7 corresponds to SEQ ID NO: 1 (SEQ1 of WO00/21995) with the His-tag removed and the KDEL amino acid sequence restored, but no other changes from SEQ1 of WO00/21995. This protein proved very difficult to purify, the final protein purity was <90% and the endotoxin load was too high for clinical use. This demonstrates that it is difficult to provide an analogue of native BiP which is easy to prepare, stable and has biological activity, as well as being suitable for administration to humans.

Four trial batches were prepared to try and improve the yield, purity and reduction in endotoxin contamination of pure protein. This proved impossible. The recovery of the protein was about 1% but endotoxin levels remained high.

Example 2

A comparison of TNFα production induced by proteins of SEQ ID NO: 3 and SEQ ID NO: 1 is provided in FIGS. 10A-10F. Peripheral blood mononuclear cells (PBMC) from 4 healthy controls (solid symbols) and 1 rheumatoid arthritis patient (open symbol) were cultured for 24 h in the presence of SEQ ID NO: 1 or SEQ ID NO: 3. Cytokines produced in the supernatant were detected and quantified by ELISA.

TNFα production by PBMC is greatly reduced in the presence of SEQ ID NO: 3 as compared to SEQ ID NO: 1. Furthermore, the protein of the invention does not increase the production of TNFα by rheumatoid arthritis PBMC differently to healthy controls, whereas the protein of SEQ ID NO: 1 appears to induce greater production of TNFα by the RA PBMC than the healthy PBMC.

The clinical significance of TNFα in the pathogenesis of rheumatoid arthritis (RA) is well established (see Role of cytokines in rheumatoid arthritis: an education in pathophysiology and therapeutics, Feldmann M, Maini S R, Immunol Rev. 2008 Jun; 223:7-19). It is therefore an important positive feature of the protein of the invention that it does not upregulate TNFα.

Example 3

The interaction between the molecules that regulate T cell activation is complex but since rheumatoid arthritis is a disease of chronic inflammation these molecules and their relative expression are important. Human Leukocyte Antigen-antigen D Related (HLA-DR) is a molecule constitutively expressed by monocytes, macrophages and dendritic cells, generally known as antigen presenting cells, each of which holds an antigenic peptide ready to be presented to the CD4+ T cell receptor. However for full T cell activation two signals are required one through HLA-DR-T cell receptor ligation and a simultaneous second signal through CD28 via CD86 or CD80 ligation. The second signal is provided by costimulatory molecules CD86 and/or CD80, also expressed by the antigen presenting cells, initially binding to CD28, expressed by the CD4 T cell which is later downregulated while CTLA-4 is upregulated. The activation of the T cell is regulated by the expression of these molecules. CD28 gives a positive activation signal while CTLA-4 gives a negative signal to the T cell. CTLA-4 also binds CD80 and CD86 with greater avidity than CD28, this has the effect of inhibiting T cell activation thus preventing chronic or continued T cell activation.

The interaction of these four molecules helps to regulate the immune response. Thus, it is notable that SEQ ID NO: 1 showed down-regulation of CD86 and also HLA-DR. This acted to reduce T cell activation, illustrated by a reduced in vitro response of BiP-treated PBMC to recall antigen, such as tuberculin PPD but also signals the possibility of generalised immunosuppression which would not be clinically beneficial in the long-term (Michael Dandel, Hans Brendan Lehmkuhl, Christoph Knosalla, Roland Hetzer, Impact of different long-term maintenance immunosuppressive therapy strategies on patients' outcome after heart transplantation, Transplant Immunology; Volume 23, Issue 3, July 2010, Pages 93-103), see FIG. 11D. In contrast, SEQ ID NO: 3 in accordance with the invention caused no significant loss of HLA-DR (FIG. 11E) and CD86 expression.

FIGS. 11A-11E shows the results of flow cytometry experiments on CD14+ cells. In the presence of SEQ ID NO: 3 (FIG. 11B there is an increase in the expression of CD80 and an increase in CD86 relative to unstimulated cells (FIG. 11A). In the presence of SEQ ID NO: 1 (FIG. 11C) there is an increase in expression of CD80 but not CD86 relative to unstimulated cells.

In conclusion, this reveals two important points of interest. Firstly, that although a reduction in T cell activation would reduce inflammation, as seen with SEQ ID NO: 1, a general suppression of the immune system is not beneficial for the patient in the long term, leading to increased infection etc. Secondly, SEQ ID NO: 3 in accordance with the invention has already shown anti-inflammatory efficacy in in vivo models. This demonstrates modulation of the immune system to resolve chronic inflammation through BiP specific activity avoiding a generalised immunosuppressive effect.

Example 4: Clinical Data

The results from a randomised placebo-controlled, dose ascending double blind phase I/II clinical trial, in patients with active RA who had failed accepted therapies, showed that the protein of the invention is safe. Furthermore, biomarker analysis showed considerable anti-inflammatory activity with clinical benefit (see Kirkham B, Chaabo K, Hall C, Garrood T, Mant T, Allen E, et al. Safety and patient response as indicated by biomarker changes to binding immunoglobulin protein in the phase I/IIA RAGULA clinical trial in rheumatoid arthritis, Rheumatology 2016; 55:1993-2000.)

Twenty-four patients with active RA who were not responsive to treatment with one or more disease-modifying anti-rheumatic drugs (DMARDs) were sequentially assigned to three groups each of eight patients randomly allocated to receive placebo (two patients) or the protein of SEQ ID NO: 3 in accordance with the invention (six patients), in doses of 1, 5 or 15 mg. Patients received a single i.v. infusion over 1 h and were observed as inpatients overnight. Patients were monitored over the following 12 weeks with follow-up clinical and laboratory assessments for safety, efficacy (DAS28-ESR) and biomarker analysis.

Safety

No infusion reactions or serious adverse drug reactions were noted. Adverse events were evenly distributed between placebo and active groups with no drug-related toxicities. Haematological, renal and metabolic parameters showed no drug-related toxicities.

Efficacy

The disease activity score (DAS28) has been developed as a dynamic assessment tool and a therapeutic response measure for use in clinical trials and practice. DAS28-ESR uses the following disease indicators: tender joint count (28 joints), swollen joint count (28 joints), Erythrocyte Sedimentation Rate (ESR) and patient-reported general health status on a 100 mm visual analogue scale, see Prevoo, M L et al, Arthritis Rheum 1995; 38:44-8.

The main efficacy end point was DAS28-ESR response, graded according to the EULAR response criteria into good, moderate and non-response with remission defined as a DAS28-ESR of less than 2.6 (Kirkham B, Chaabo K, Hall C, Garrood T, Mant T, Allen E, et al. Safety and patient response as indicated by biomarker changes to binding immunoglobulin protein in the phase I/IIA RAGULA clinical trial in rheumatoid arthritis. Rheumatology 2016; 55:1993-2000). Biological efficacy endpoints were changes in CRP (FIG. 12), IL-8 and VEGF (FIGS. 13A-13B), see further discussion below. These are commonly used to monitor disease activity in clinical drug trials of treatments for rheumatoid arthritis.

Clinically, good EULAR responses were more common in those treated with higher doses of SEQ ID NO: 3 with sustained low DAS28 scores (from 3 to 12 weeks) observed in three patients who received SEQ ID NO: 3, compared with no patients who received placebo, although good DAS28-ESR responses were achieved in all treatment groups.

Serum VEGF and IL-8 Concentration

FIGS. 13A-13B show the change in serum levels of VEGF or IL-8 in the presence of SEQ ID NO: 3 from the pre-infusion baseline for each patient at 2 weeks or 12 weeks measured by Luminex technology (Bio-Rad, Hemel Hempstead, UK). Only patients remaining in the study at 12 weeks were included in this analysis (FIGS. 13A-13B).

Analysis of CRP, VEGF and IL-8 proved useful in differentiating subjects receiving active drug compared with placebo. Patients who responded to SEQ ID NO: 3 showed a significant decrease in CRP at 2 weeks (pre-infusion level, 12.7±1.7 versus 2 week post infusion level, 7.1±2.1; p=0.02), compared with the placebo and non-responder groups. Serum VEGF and IL-8 are common biomarkers used in clinical trials because they correlate well with measurement of synovitis and monocyte infiltration respectively. Significant changes in levels of these bio-markers occurred in patient groups receiving SEQ ID NO: 3. Furthermore, biomarkers did not support clinical improvement in placebo patients. Strikingly, at week 12 significantly fewer patients who received placebo showed reduced serum VEGF and IL-8 (17 and 50%, respectively), compared with the SEQ ID NO: 3 responder group (71 and 83% of patients, respectively). Interestingly even the SEQ ID NO: 3 non-responder group showed reduced serum concentrations (66 and 83% of patients, respectively), suggesting a change in the pathology of their disease.

In summary, the active responding patients showed significantly lower serum concentrations of CRP, 2 weeks post-infusion compared with pre-infusion levels (FIG. 12), and of VEGF and IL-8 (FIGS. 13A-13B) from the placebo group. This indicates that the disease inflammation is considerably less than pre-infusion levels.

Example 5: SEQ ID NO: 3 Upregulates CD39 on Regulatory T Cells

Peripheral blood mononuclear cells from an RA patient were set up in culture either unstimulated (open bars) or with SEQ ID NO: 1 (10 μg/ml) (crosshatched bars) or SEQ ID NO: 3 (10 μg/ml) (black bars, FIGS. 14A-14D).

After 24 h, 48 h or 72 h cells were removed from culture and stained with a panel of fluorochrome conjugated antibodies for CD45, CD3, CD4, CD25, CD127 and CD39. Cells were analysed on a FACSCanto flow cytometer (BD Biosciences).

Results in FIGS. 14A-14D are expressed as the mean fluorescent intensity (MFI) for:

(A) CD25 hi and CD127lo cells after using multiple live gates to access live, CD45+, CD3+, CD4+ cells;
(B) the expression of CD39 on the CD45+CD3+CD4+ CD25hiCD127lo population in (A).
(C) PBMC (106/ml) were pre-treated for 96 h in culture with SEQ ID NO: 1 (10 or 0.1 μg/ml) or SEQ ID NO: 3 in accordance with the invention (10 or 0.1 μg/ml), washed and added to fresh autologous CFSE stained (the cytoplasmic dye carboxyfluorescein diacetate succinimidyl ester) T cells and stimulated with anti-CD3 and anti-CD28 antibody coated beads. The ratio of pre-treated T cells to responder T cells was 1:10. The cells were analysed for reduction in CFSE MFI using Cellquest software on a FACS Calibur after 3 days. As cells proliferate the CFSE content is reduced by each division and cells that do not proliferate remain highly stained.
(D) In the clinical trial, whole blood samples from placebo and SEQ ID NO: 3 treated rheumatoid arthritis patients, responder (R) or non-responder (NR), were monitored for the change in expression of CD39 on Treg cells (live, CD45+CD3+CD4+CD25 hi CD127lo) over 12 weeks. Results are expressed as a % change in cell surface expression at the indicated time-points, from pre-infusion.

The in vitro comparison between SEQ ID NO: 1 and SEQ ID NO: 3 in accordance with the invention shows that although the actual increase in Treg number is low, thus confirming previous work with SEQ ID NO: 1, there is a greater difference in the % expression of CD39 on the Treg with SEQ ID NO: 3 when compared directly with SEQ ID NO: 1. Of interest is that at 72 h the CD39 expression on Treg from the SEQ ID NO: 1 cultures is lower than that of the control cells. In the clinic a significant increase in the expression of CD39 on Treg cells from patients responding to SEQ ID NO: 3 was observed and this was maintained for 12 weeks post-infusion.

Figure 15:
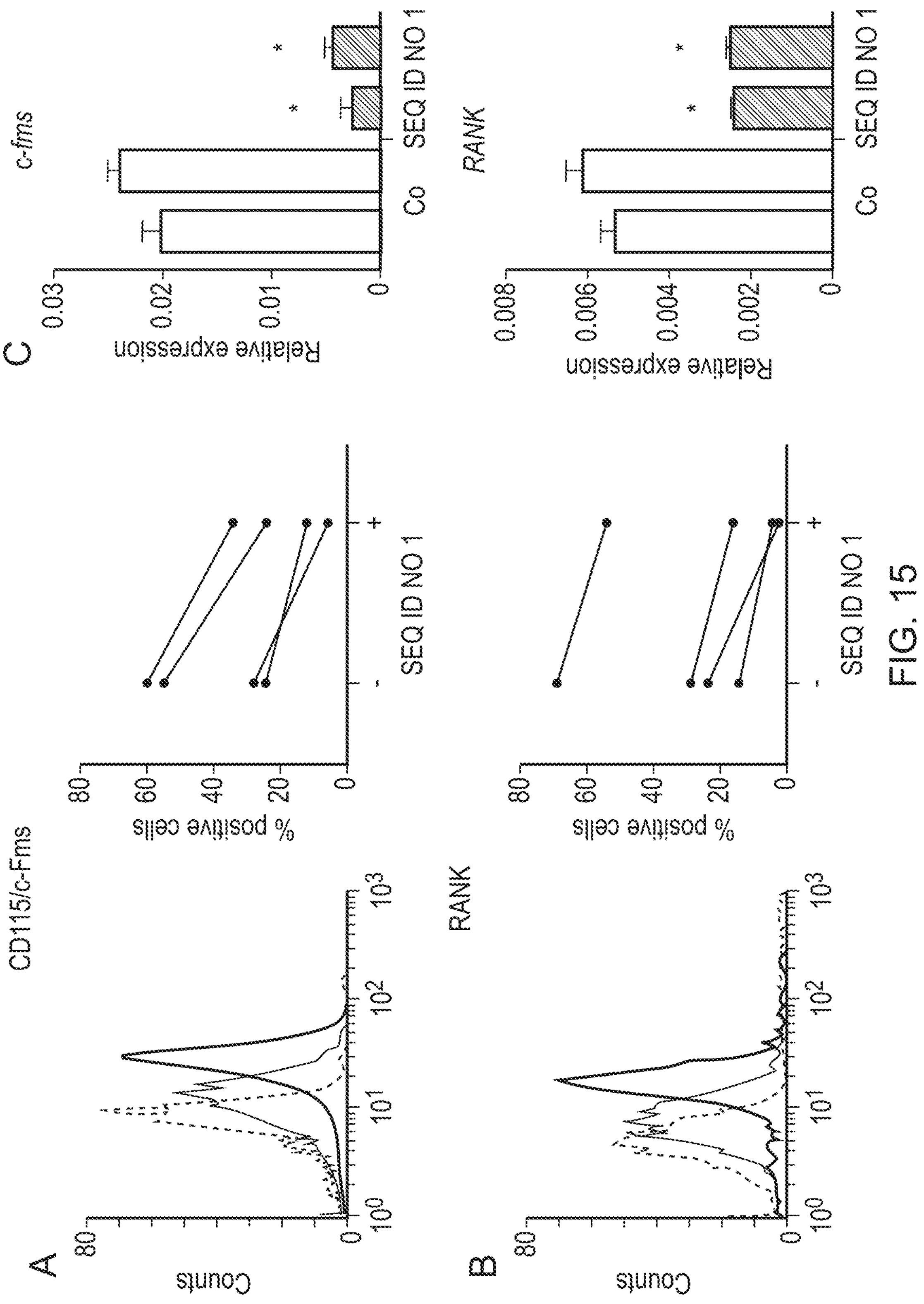
Figure 15:
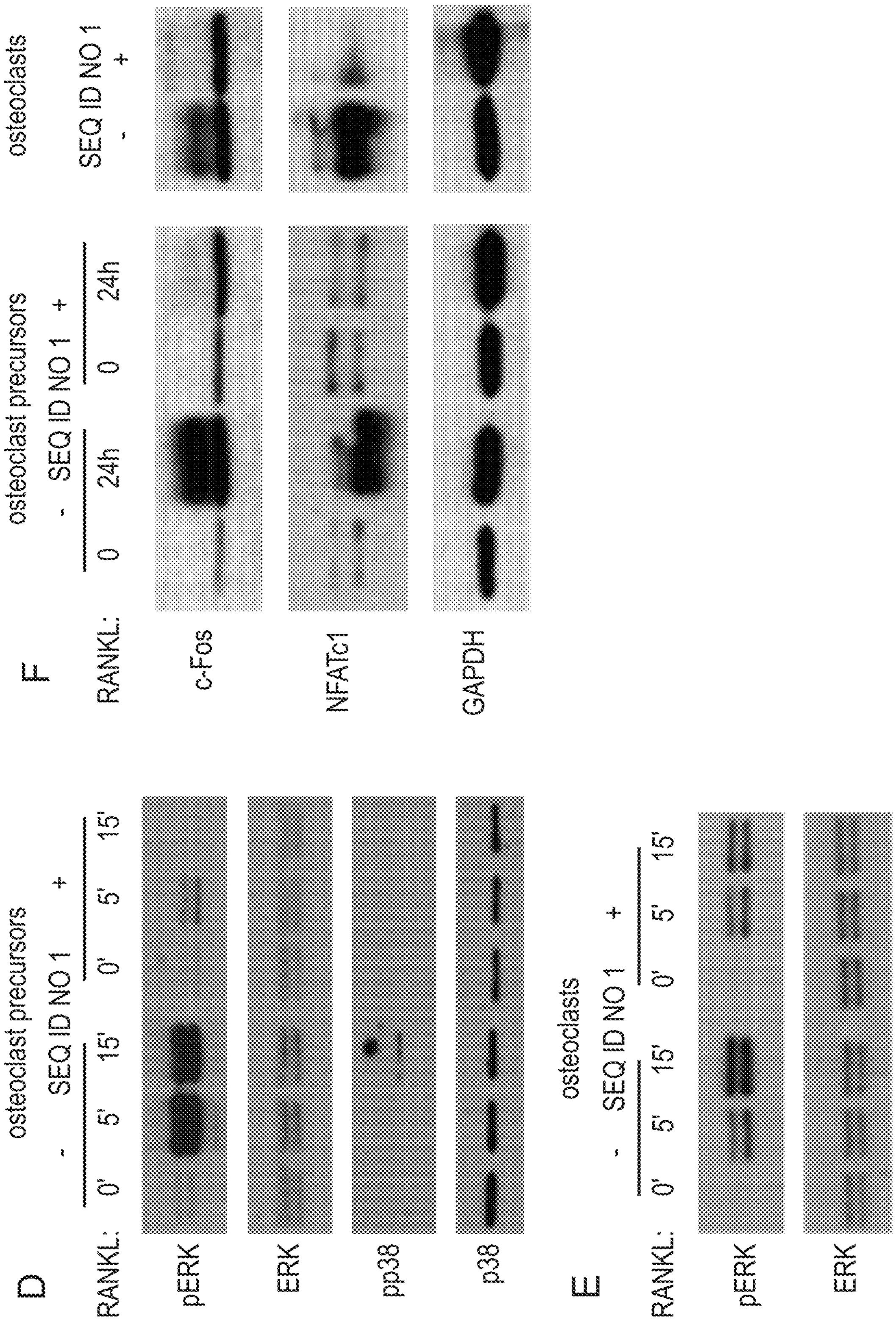

Example 6: SEQ ID NO: 3 Suppresses Osteoclast Differentiation Signaling Pathways To investigate the mechanisms underlying the inhibition of osteoclastogenesis by SEQ ID NO: 1 and SEQ ID NO: 3, we analyzed specific cytokine signaling and downstream signaling pathways known to be essential for osteoclast differentiation. Flow cytometric analysis of CD115/c-Fms and RANK, the receptors for M-CSF and RANKL respectively, in human peripheral blood derived M-CSF-dependent osteoclast precursors revealed that SEQ ID NO: 3 down-regulated the expression of CD115 by 63±16% (range of inhibition, 43-79%) (FIG. 15A). SEQ ID NO: 1 similarly inhibited RANK protein expression by 51±29% (range of inhibition, 22-90%) (FIG. 15B). The inhibition of c-Fms and RANK expression was also observed at the mRNA level, as qPCR analysis showed significant reductions in c-fms and RANK RNA (FIG. 15C). To address whether the decrease in receptor expression resulted in reduced responsiveness to osteoclastogenic cytokines, we analyzed the effect of SEQ ID NO: 1 treatment on RANKL-dependent MAPK signaling. Pre-treatment of human PBMC-derived osteoclast precursors with SEQ ID NO: 1 markedly suppressed RANKL-induced ERK and p38 phosphorylation compared to untreated cells (FIG. 15D). Similar results were obtained using M-CSF-dependent murine bone marrow-derived osteoclast precursors (data not shown). Further examination of RANKL responsiveness in late-stage cultures similarly revealed that RANKL-induced PERK levels were also attenuated in cultures enriched in mature osteoclasts following SEQ ID NO: 1 treatment (FIG. 15E).

We next investigated the effect of SEQ ID NO: 1 on the expression of the transcription factors c-Fos and NFATc1, which are essential for osteoclast differentiation and which lie downstream of RANK and TNFα signaling in osteoclast precursors and monocytes. Pre-incubation of human osteoclast precursors with SEQ ID NO: 1 greatly reduced the activation of c-Fos protein following RANKL treatment (FIG. 15F). RANKL stimulation of NFATc1, a c-Fos target gene, was similarly blocked in osteoclast precursors treated with SEQ ID NO: 1 when compared to control cell lysates (FIG. 15F). Mature osteoclast cultures treated with SEQ ID NO: 1 also showed a marked decrease in the endogenous expression of both c-Fos and NFATc1 transcription factors (FIG. 15F).

Since SEQ ID NO: 1 inhibits the signalling pathways required for the differentiation of monocytes to osteoclasts, we looked to see if SEQ 3 would have a similar effect on NF-κB one of the transcription factor that drives inflammation but the alternative pathway is required by RANK-RANKL to drive downstream differentiation.

Imaging flow cytometry demonstrated that SEQ ID NO: 3 treatment inhibited the TNFα-induced nuclear translocation of p65 NF-κB in osteoclast precursors (FIG. 16A). Similar results were obtained in response to RANKL stimulation (data not shown). Since RANKL also stimulates cells via the non-canonical NF-κB pathway, we investigated the nuclear translocation of p52 NF-κB following RANKL stimulation. Confocal microscopy and image analysis showed that whereas RANKL stimulated efficient nuclear translocation of p52 in untreated cells, this was inhibited by SEQ ID NO: 3 pretreatment (FIG. 16B). These results suggest that SEQ ID NO: 3 blocks both canonical as well as non-canonical NF-κB signaling in monocytes and osteoclast precursors following TNFα and RANKL treatment.

Taken together, these data demonstrate that treatment of monocytes and osteoclast precursors with SEQ ID NO: 3 reduces M-CSF- and RANKL-induced signal transduction and activation of the essential osteoclastogenic transcription factors NF-κB, c-Fos and NFATc1, thereby providing insights into the mechanisms whereby SEQ ID NO: 3 inhibits osteoclast differentiation and resorptive activity.

This data provides evidence that SEQ ID NO:3 can be used to treat diseases of dysregulated bone metabolism.

Example 7

Following treatment with SEQ ID NO: 3 or placebo the immune response of patients was measured using PBMC culture stimulated to detect T cell responses to a maximal stimulus, anti-CD3 and anti-CD28 antibody coated beads (3 day culture) (FIG. 17A) or recall antigen, tuberculin PPD (5 day culture) (FIG. 17B).

Activation was measured by uptake of tritiated thymidine by proliferating cells for the last 24 h of culture. The data show no change in response to mitogen or recall antigen over the 12 weeks of the clinical trial. This indicates that SEQ ID NO: 3 has no overall immunosuppressive effect, unlike SEQ ID NO: 1 which has already been published as reducing the recall antigen response to tuberculin PPD (Corrigall V M, Bodman-Smith M D, Brunst M, Cornell H, Panayi G S. The stress protein, BiP, stimulates human peripheral blood mononuclear cells to express an anti-inflammatory cytokine profile and to inhibit antigen presenting cell function: relevance to the treatment of inflammatory arthritis. Arthritis Rheum 2004; 50:1167-1171).

Example 8: Transplantation; Mouse Model of Skin Grafts

FIGS. 18A-18B show a schematic representation of the protocol and results of a murine skin transplantation experiment: All recipient mice were administered anti-CD8 antibody to deplete endogenous dendritic cells eight days before transplantation. There were 6 mice in each of four groups. Seven days prior to transplantation control mice received vehicle only. SEQ ID NO: 3 (20 μg/mouse) was administered intravenously. Two other groups received immature or mature plasmacytoid dendritic cells from H2Kb matched mice. After 1 week small pieces of skin from the tail of H2Kd mismatched mice were transplanted onto the back of the recipient mice.

Graft survival analysis by Kaplan Meier graph shows that SEQ ID NO: 3 extended the survival of 5/6 of the grafts beyond that of the control group with 50% grafts surviving for approximately 30% longer than the control mice grafts.

The data presented shows that SEQ ID NO: 3 is effective at maintaining graft survival in the mouse model of skin grafts, a model reputed to be highly difficult to maintain graft survival.

A second transplantation exploratory experiment was also carried out (see FIG. 19). Again, SEQ ID NO: 3 administration leads to longer survival of skin grafts in comparison with those animals given modified dendritic cells (DC). Mixing DC administration with SEQ ID NO: 3 was not beneficial.

Example 9: Prosthetic Joint Loosening

On prosthesis loosening the tissue which develops around the prosthetic joints, peri-prosthetic tissue, is very similar to synovial membrane which becomes inflamed during RA. This tissue can cause loosening of the prosthetic joint. Peri-prosthetic tissue (PPT) was collected during revision surgery for prosthetic joint replacements. Tissue was cut into small pieces of equal weight and cultured overnight in tissue culture medium (1 ml) in twenty-four well plates in the presence or absence of SEQ ID NO: 3. Culture supernatants were collected between 24 h-72 h and TNFα, pro-inflammatory, or interleukin-10, anti-inflammatory, cytokines were quantified by commercial enzyme linked immunosorbent assay (ELISA) (PharMingen, BD, Oxford, UK)

FIGS. 20A-20B shows that although the protein of the invention had little effect on the production of TNFα, IL-10 was markedly increased.

The data provided by the inventors demonstrates that SEQ ID NO:3 has a significant anti-inflammatory effect. This indicates that SEQ ID NO: 3 can be used to treat inflammatory bowel disease, for example Crohn's disease.

Example 10

Tables 4 and 5 summarises the physical and functional differences between the protein of the invention, SEQ ID NO: 1 and native BiP. This clearly summarises the significant differences between the protein of the invention, the previously published recombinant BIP SEQ ID NO: 1, and the native protein.

TABLE 4

| | Protein Source | Molecule appearance | Glycosylation | 5' terminal sequence | 3' terminal sequence | Surface expression |
|---|---|---|---|---|---|---|
| Native intracellular | Human | Mono - oligo | Yes | EEED | KDEL | No |
| SEQ ID NO: 1 | Bacterial | Mono (10%) <dimer (90%) | No | MEED | LHHHHHH | N/A |
| SEQ ID NO: 3 | Bacterial | Monomer | No | RAEEED | KDEL | N/A |

TABLE 5

| Protein | Protein Function | | | | | | |
|---|---|---|---|---|---|---|---|
| | Protein source | TNF production | IL-10 production | CD86 expression | HLA-DR expression | Effect on tuberculin PPD T cell response | Induction of Treg |
| SEQ ID NO: 1 | Bacterial | ++ | +++ | ↓↓ | ↓↓ | ↓↓ | + CTLA-4 + CD39CD4 |
| SEQ ID NO: 3 | Bacterial | ± | + | ↔ | ↔ | ↔ | + CTLA-4 ++ CD39 CD4CD25hi CD127lo +++ CD39 CD4CD25hi CD127lo clinic |

| Protein | Protein Function | | | | | | |
|---|---|---|---|---|---|---|---|
| | Induction IDO+ DC | NFKB activation In various cells | CIA therapy | Recovery from arthritis (CIA) | Inhibition of osteoclast differentiation and function | IFNγ production (CIA) | IFNγ production (clinical trial) |
| SEQ ID NO: 1 | ++ | ↓ | Yes | Yes* | Yes | ↔ | |
| SEQ ID NO: 3 | | ↓↓ | Yes | Yes** Clinical trial remission | Yes | | ↓↓ |

Chick collagen model improved severe arthritis n = 1;
**reduction of DAS28 in clinical trial, CIA = Collagen Induced Arthritis All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The invention claimed is:

1. A method of treating a condition in a human subject, the condition being characterized by excessive osteoclastogenesis and/or bone resorption, the method comprising administering to the subject a therapeutically-effective amount of an isolated or recombinant protein comprising or consisting of the amino acid sequence selected from SEQ ID NO: 3 or SEQ ID: NO: 4, wherein the condition is selected from the group consisting of osteoporosis, Paget's disease, and bone loss associated with cancer, and wherein the administration reduces M-CSF signaling, reduces RANKL signaling, and reduces activation of essential osteoclastogenic transcription factors NF-κB, c-Fos and NFATc1 in osteoclast precursors and reduces osteoclast differentiation and/or reduces bone resorptive activity in the subject.

2. The method of claim 1, wherein the condition is bone loss associated with metastatic breast cancer.

3. The method of claim 1, wherein the protein is SEQ ID NO:3.

4. The method of claim 1, wherein the protein is SEQ ID NO:4.

5. The method of claim 1, wherein the administration reduces expression of c-Fms and/or RANK in osteoclast precursors.

6. The method of claim 1, wherein the administration inhibits nuclear translocation of NF-κB p65 and/or p52 in osteoclast precursors.

* * * * *